US008247563B2

(12) United States Patent
Bhat et al.

(10) Patent No.: US 8,247,563 B2
(45) Date of Patent: Aug. 21, 2012

(54) COMPOSITIONS, SYNTHESIS, AND METHODS OF USING INDANONE BASED CHOLINESTERASE INHIBITORS

(75) Inventors: Laxminarayan Bhat, Cupertino, CA (US); Prabhu Prasad Mohapatra, San Jose, CA (US)

(73) Assignee: Reviva Pharmaceuticals, Inc., San Jose, CA (US)

( * ) Notice: Subject to any disclaimer, the term of this patent is extended or adjusted under 35 U.S.C. 154(b) by 1148 days.

(21) Appl. No.: 12/001,582

(22) Filed: Dec. 11, 2007

(65) Prior Publication Data

US 2008/0153878 A1    Jun. 26, 2008

Related U.S. Application Data

(60) Provisional application No. 60/869,499, filed on Dec. 11, 2006.

(51) Int. Cl.
*C07D 401/00* (2006.01)
*A61K 31/445* (2006.01)
(52) U.S. Cl. .................................... 546/201; 514/323
(58) Field of Classification Search .............. 546/201; 514/323
See application file for complete search history.

(56) References Cited

U.S. PATENT DOCUMENTS

| | | | |
|---|---|---|---|
| 3,845,770 | A | 11/1974 | Theeuwes et al. |
| 3,916,899 | A | 11/1975 | Theeuwes et al. |
| 4,668,687 | A | 5/1987 | Yevich et al. |
| 4,895,841 | A | 1/1990 | Sugimoto et al. |
| 5,100,901 | A | 3/1992 | Sugimoto et al. |
| 5,112,598 | A | 5/1992 | Biesalski |
| 5,272,158 | A * | 12/1993 | Hartman et al. ............. 514/323 |
| 5,556,611 | A | 9/1996 | Biesalski |
| 5,606,064 | A | 2/1997 | Lensky |
| 5,696,070 | A | 12/1997 | Tachizawa et al. |
| 5,698,155 | A | 12/1997 | Grosswald et al. |
| 6,252,081 | B1 | 6/2001 | Iimura |
| 6,413,986 | B1 * | 7/2002 | Kosley et al. ............... 514/319 |
| 6,514,984 | B1 | 2/2003 | Watanabe |
| 2004/0143121 | A1 | 7/2004 | Reddy et al. |
| 2004/0158070 | A1 | 8/2004 | Radhakrishnan et al. |

FOREIGN PATENT DOCUMENTS

| | | |
|---|---|---|
| EP | 0042322 A1 | 12/1981 |
| EP | 0535496 A1 | 4/1993 |
| EP | 1116716 A1 | 7/2001 |
| EP | 1157989 A1 | 11/2001 |
| EP | 1209151 A1 | 5/2002 |
| EP | 1260512 A1 | 11/2002 |
| EP | 1468684 A1 | 10/2004 |
| WO | WO 00/09483 A3 | 2/2000 |
| WO | WO 01/32115 A1 | 5/2001 |
| WO | WO 2005/003092 A1 | 1/2005 |
| WO | WO 2005/076749 A2 | 8/2005 |
| WO | WO 2007/052541 A1 | 5/2007 |
| WO | WO 2007/077443 A1 | 7/2007 |

OTHER PUBLICATIONS

PCT International Search Report and Written Opinion, PCT/US07/25392, Apr. 25, 2008, 8 pages.
Cardozo, M.G. et al., "Confirmational Analysis and Molecular-Shape Comparisons of a Series of Indanone-Benzylpiperidine Inhibitors of Acetylcholinesterase," Journal of Medicinal Chemistry, Jun. 19, 1992, pp. 590-601, vol. 35.
European Extended Search Report, European Application No. 07867720.0, Apr. 27, 2011, 11 pages.
Sugimoto, H. et al., "Synthesis and Structure-Activity Relationships of Acetylcholinesterase Inhibitors: 1-Benzyl-4-[(5,6-dimethoxy-1-oxoindan-2-yl)methyl]piperidine Hydrochloride and Related Compounds," Journal of Medicinal Chemistry, Nov. 24, 1995, pp. 4821-4829, vol. 38, No. 24.
Goodson, J.M. "Medical Applications of Controlled Release," Langer, R.S. et al., eds., 1984, pp. 115-138.
Langer, R., "New Methods of Drug Delivery," Science, Sep. 28, 1990, pp. 1527-1533, vol. 249.
New Zealand Examination Report, New Zealand Patent Application No. 578187, Sep. 3, 2010, 2 pages.
Abe, T. et al., *Large Scale Synthesis of N-benzyl-4-formylpiperidine Through Partial Reduction of Esters Using Aluminum Hydride Reagents Modified with Pyrrolidine*, Tetrahedron, 2001, pp. 2701-2710, vol. 57.
During, M.J. et al., *Controlled Release of Dopamine from a Polymeric Brain Implant: In Vivo Characterization*, Annals of Neurology, 1989, pp. 351-356, vol. 25, No. 4.
Eaton, P.E. et al., *Phosphorus Pentoxide-Methanesulfonic Acid. A Convenient Alternative to Polyphosphoric Acid*, Journal of Organic Chemistry, 1973, pp. 4071-4073, vol. 38, No. 23.
Fillion, E. et al., *Meldrum's Acids as Acylating Agents in the Catalytic Intramolecular Friedel—Crafts Reaction*, Journal of Organic Chemistry, 2005, pp. 1316-1327, vol. 70, No. 4.
Howard III, M.A. et al., *Intracerebral Drug Delivery in Rats with Lesion-Induced Memory deficits*, Journal of Neurosurgery, Jul. 1989, pp. 105-112, vol. 71.
Langer, R. et al., *Chemical and Physical Structure of Polymers as Carriers for Controlled Release of Bioactive Agents: A Review*, Polymer Reviews, 1983, pp. 61-126, vol. 23, Issue 1.
Levy, R.J. et al., *Inhibition of Calcification of Bioprosthetic Heart Valves by Local Controlled-Release Diphosphonate*, Science, Apr. 1985, pp. 190-192, vol. 228, No. 4696.
Miwa, K. et al., *Extension of the Colvin Rearrangement Using Trimethylsilyldiazomethane. A New Synthesis of Alkynes*, Synlett, 1994, pp. 107-108, No. 2.
Premasagar, V. et al., *Methanesulfonic Acid Catalyzed Cyclization of 3-Arylprpanoic and 4-Arylbutanoic Acids to 1-Indanones and 1-Tetralones*, Journal of Organic Chemistry, 1981, pp. 2974-2976, vol. 46.
Saudek, C.D. et al., *A Preliminary Trial of the Programmable Implantable Medication System for Insulin Delivery*, The New England Journal of Medicine, Aug. 31, 1989, pp. 574-579, vol. 321, No. 9.
Sefton, M.V., Implantable Pumps, CRC Critical Reviews in Biomedical Engineering, 1987. pp. 201-240, vol. 14.

(Continued)

*Primary Examiner* — Janet Andres
*Assistant Examiner* — John Mabry
(74) *Attorney, Agent, or Firm* — Perkins Coie LLP.; Viola T. Kung

(57) ABSTRACT

The present invention provides novel indanone derivatives which can be advantageously used for treating and/or preventing of a medical condition for which inhibition of a cholinesterase is desired.

10 Claims, No Drawings

OTHER PUBLICATIONS

Shah, R.R., *Pharmacogenetics in Drug Regulation: Promise, Potential and Pitfalls*, Philosophical Transactions of the Royal Society, 2005, pp. 1617-1638, vol. 360.

Sugimoto, H. et al., *Synthesis and Structure—Activity Relationships of Acetylcholinesterase Inhibitors: 1-Benzyl-4(2-phthalimidoethy) piperidine and Related Derivatives*, Journal of Medical Chemistry., 1992, pp. 4542-4548, vol. 35, No. 24.

Sugimoto, H. et al., *Synthesis and Structure—Activity Relationships of Acetylcholinesterase Inhibitors: 1-Benzyl-4-[(5,6-dimethoxy-1-oxoindan-2-yl)methyl] piperidine Hydrochloride and Related Compounds*, 1995, Journal of Medical Chemistry, pp. 4821-4829, vol. 38, No. 24.

Verma, R.K. et al., *Osmotically Controlled Oral Drug Delivery*, Drug Development and Industrial Pharmacy, 2000, pp. 695-708, vol. 26, No. 7.

New Zealand Examination Report, New Zealand Application No. 578187, Oct. 4, 2011, 2 pages.

\* cited by examiner

COMPOSITIONS, SYNTHESIS, AND METHODS OF USING INDANONE BASED CHOLINESTERASE INHIBITORS

CROSS-REFERENCE TO RELATED APPLICATIONS

This application claims the benefit of U.S. Provisional Patent Application No. 60/869,499, filed on Dec. 11, 2006, and which is herein incorporated by reference in its entirety.

FIELD OF THE INVENTION

The present invention relates to compositions of indanone derivatives, synthesis of indanone derivatives, and methods of using indanone derivatives. The present invention more particularly relates to synthesis, compositions and methods of using indanone based compounds which are useful for treating and/or preventing a medical condition for which a cholinesterase inhibitor is desired.

BACKGROUND OF THE INVENTION

Cholinesterase is needed for the proper functioning of the nervous systems of humans. If the amount of cholinesterase is reduced below a critical level, nerve impulses to the muscles can no longer be controlled, resulting in serious consequences and even death. The term cholinesterase is generally referred to one of the two enzymes: acetylcholinesterase (AChE) and butyrylcholinesterase (BChE or BuChE). Acetylcholinesterase (AChE), also known as RBC cholinesterase, erythrocyte cholinesterase, or (most formally) acetylcholine acetylhydrolase, is found primarily in the blood and neural synapsases. Butyrylcholinesterase (BuChE), also known as pseudocholinesterase, plasma cholinesterase, or (most formally) acylcholine acylhydrolase, is found primarily in the liver. Both of these enzymes catalyze the hydrolysis of the neurotransmitter acetylcholine into choline and acetic acid, a reaction necessary to allow a cholinergic neuron to return to its resting state after activation.

Acetylcholinesterase (AChE) is a tetrameric protein which catalyzes the hydrolysis of the neurotransmitter acetylcholine (a chemical released by nerves that activates muscle contractions) and helps to maintain proper transmission of impulses between nerve cells and between nerve cells and muscles. A variety of neurological and neuromuscular disorders or diseases involve a diminution of cholinergic activity. Often the most effective treatments for such disorders or diseases involve use of a cholinesterase inhibitor which inhibits the breakdown of acetylcholine. A cholinesterase inhibitor or anticholinesterase is a chemical or a ligand that inhibits a cholinesterase enzyme from breaking down acetylcholine, so increasing both the level and duration of action of the neurotransmitter acetylcholine. Acetylcholinesterase inhibitors have been used clinically in the treatment of Alzheimer's disease or Alzheimer type dementia, Huntington's disease, Pick's disease, ataxia, myasthenia gravis (a degenerative neuromuscular disorder) and glaucoma.

Alzheimer's disease or Alzheimer type dementia (also called as Senile Dementia of the Alzheimer Type) is a progressive illness that kills nerve cells and destroys nerve connections in the brain. The disease is marked by mental changes resulting from damage in the brain tissue. Because these changes cannot be visualized until autopsy, diagnosis for the disease is based on symptoms that patients have. Symptoms include gradual loss of awareness, memory, and judgment as well as mood and behavioral disturbances. While the exact cause of this disease is still unknown, researchers have found several factors that may contribute to the development of the disease, including an inflammatory response, genetic factors, and environmental influences.

Prevalence of Alzheimer's disease across the world is unknown. However, recent reports suggest that about 4.5 million Americans have Alzheimer's disease. It is estimated that by the year 2050 this number will be greater than 13 million because the baby boomers will by that year be over the age of 65. Alzheimer's disease is the leading cause of dementia (the loss of healthy mental function) and the eighth leading cause of death in the United States. The lifespan of an Alzheimer's disease victim is generally reduced, although a person may live anywhere from 3 to 20 years after diagnosis.

Alzheimer's disease is not reversible and currently there is no cure for this disease. The pharmacological treatments currently available are mainly aimed at alleviating or improving symptoms of the disease. Cholinesterase inhibitors are commonly prescribed and are the only agents approved by the FDA for the treatment because they have been shown to minimize and stabilize the symptoms of Alzheimer's disease. The FDA approved cholinesterase inhibitors are donepezil (Aricept®), tacrine (Cognex®), rivastigmine (Exelon®), and galantamine (Reminyl®). Clinical trials show that these drugs can stabilize or improve cognition, global assessment scores, mood and behavior in people with Alzheimer's disease. In recent years, Donepezil (Sugimoto et al. U.S. Pat. No. 4,895,841 and 5100901; Pathi et al. WO 2007077443; Parthasaradhi et al. WO 2005003092; Dubey et al. WO 2005076749; Gutman et al. WO 200009483; Sugimoto et al. J Med Chem 1995, 38, 481) has been used as a first-line therapy for the treatment of Alzheimer's disease.

However, all the AChE inhibitors currently in clinical use including donepezil have notable limitations. They exhibit substantial interpatient variability in pharmacokinetics and have significant interactions with other drugs. An important reason for interpatient variability and interactions with other drugs (drug-drug interactions) involves genetically determined differences in the metabolism of these drugs. All AChE inhibitors currently in clinical use undergo significant hepatic metabolism via cytochrome P450 isoenzymes 3A4, including 2D6 and 1A2 isoenzymes except rivastigmine. Hepatic metabolism is also a key determinant of the potential for a given drug to be involved in clinically significant pharmacokinetic drug interactions (Buffum et al. Geriatric Nursing 2005, 26, 74-78). There are significant polymorphisms in patients for CYP isoenzymes CYP2D6 and CYP1A2 (Shah, R. R. Phil. Trans. R. Soc. B. 2005, 360, 1617-1638), and this polymorphism has been shown to substantially increase plasma levels of these AChE inhibitors. Therefore, poor metabolizers, who lack CYP2D6 and CYP 1A2, can be particularly predisposed to adverse drug interactions. In addition, a number of drugs that are substrates for cytochrome P450 enzyme system, including diazepam, warfarin and phenyloin are known to interact with these AChE inhibitors. Most common adverse effects reported in patients taking these AChE inhibitors include nausea, vomiting, diarrhea, and muscle cramps. Other adverse effects reported are liver disorder, arrhythmia, cardiovascular disorder, tachycardia, dizziness, abnormal gait, aggression, anxiety, anorexia, delirium, confusion, sleep disorder, cough, and dyspnea (Iimura et al. WO 2007052541).

Majority of the Alzheimer's patients are old people and are in the age group of 55 to 85 years. It has been observed that these patients have one or more health disorders other than Alzheimer's and they are most likely diabetes, cardiovascular problems (e.g., atherosclerosis, hypertension), chronic pain, asthma, and poor functioning of liver and kidney. The most concerned adverse effects of these AChE inhibitors are drug-drug interactions and cardiac liability. The CYP mediated metabolic pathways associated with these drugs are mainly responsible for the adverse effects. The majority of the drugs currently available for the treatment of diabetes, cardiovascular, asthma and chronic pain indications are metabolized by CYP enzymes. Therefore, Alzheimer's patients being treated with the AChE inhibitors are at greater risk for adverse side effects derived from drug-drug interactions. In some cases these adverse effects can become life threatening. Taken together, these clinical limitations point towards the need to develop safer therapeutic drugs for the treatment of Alzheimer's disease.

Therefore, development of a novel AChE inhibitors that preferably undergo non-CYP mediated metabolism in the body but display the same or improved therapeutic target activity as the currently available therapies would provide effective and safer medicines for the treatment of Alzheimer's disease.

SUMMARY OF THE INVENTION

The present invention relates to novel indanone derivatives, synthesis of the derivatives, compositions and methods of using indanone derivatives which are useful for treating and/or preventing a medical condition for which an acetylcholinesterase (AChE) inhibitor is desired. The present invention provides methods for synthesizing such indanone based acetylcholinesterase inhibitors. The present invention also provides methods for using indanone based acetylcholinesterase inhibitors, and composition of indanone based acetylcholinesterase inhibitors for treating Alzheimer's disease and other neurodegenerative diseases, including Huntington's disease, Pick's disease, ataxia, myasthenia gravis and glaucoma.

The compounds of the subject invention provide next generation of novel acetylcholinesterase inhibitors that are particularly effective and safer for the treatment of Alzheimer's disease. They are advantageous because of their highly desirable metabolic, pharmacokinetics and pharmacological profiles. The compounds of the invention are designed:
1) to exhibit acetylcholinesterase inhibitory activity;
2) to undergo predominantly non-oxidative or non-CYP enzyme mediated metabolism in the human body;
3) to metabolize predominantly by hydrolytic enzymes such as esterases and/or peptidases in the human body;
4) to form therapeutically inactive or least active metabolite(s) having short half life.

Thus, the compounds of the invention display the characteristics of having good acetylcholinesterase inhibitory activity, predominantly undergo non-cytochrome P450 enzymes mediated or non-oxidative metabolism and form therapeutically inactive or least active metabolites. The features like non-cytochrome P450 enzymes mediated metabolism and therapeutically inactive or least active metabolites in the compounds of subject invention can mitigate the adverse side effects that are derived from drug-drug interactions. Therefore, having these features, the compounds of the inventions are more effective and safer for the treatment of Alzheimer's disease in humans including patients who are on multiple medications for chronic diseases for example: chronic pain, diabetes, cardiovascular diseases and asthma, and have poor functioning of liver and kidney.

In one aspect, the present invention provides indanone derivatives comprising compounds of structural Formula (I):

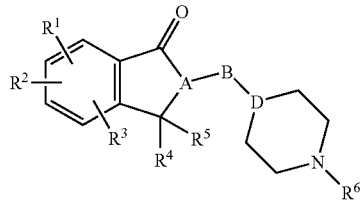

Formula I or a pharmaceutically acceptable salt, hydrate or solvate thereof provided that the compounds of the invention comprise a soft moiety conjugated directly or via a spacer onto or inserted into one of the substituents $R^1$, $R^2$, $R^3$, $R^4$, $R^5$ and $R^6$;
wherein
'A' and 'D' are independently selected to be CH, or N;
'B' is selected to be —$(CH_2)_n$—, —$(CH_2)_nC(O)$—, —$(CH_2)_n$ C(O)O—, —$(CH_2)_nOC(O)$—, —$(CH_2)_nS(O)(O)$—, —$(CH_2)_nNHC(O)$—, O, S, —C(O), —C(O)O, or —S(O) (O) wherein n=1-5;
$R^1$, $R^2$, $R^3$, $R^4$, $R^5$ and $R^6$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; preferably acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylsulfinyl, alkylsulfonyl, alkylthio, amino, alkylamino, arylalkylamino, dialkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, and sulfonamide; optionally $R^1$ and $R^2$ or $R^2$ and $R^3$ together form 5- or 6-membered ring which may contain one or more heteroatoms selected from O, N, or S and that ring may be optionally substituted with substituents selected from alkyl, substituted alkyl, halo, hydroxyl, and carbonyl; optionally $R^4$ and $R^5$ together form 5- or 6-membered ring which may contain one or more heteroatoms selected from O, N, or S and that ring may be optionally substituted with substituents selected from alkyl, substituted alkyl, halo, hydroxyl, and carbonyl.

DETAILED DESCRIPTION OF THE INVENTION

The present invention relates to synthesis, compositions and methods of using indanone derivatives which are useful for treating and/or preventing a medical condition for which inhibition of cholinesterase enzyme is desired. The present invention provides compounds, compositions and methods for pharmacological treatment of Alzheimer's disease and other neurodegenerative diseases, including Huntington's disease, Pick's disease, ataxia, myasthenia gravis and glaucoma.

Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "Advanced Organic Chemistry 3$^{rd}$ Ed." Vols. A and B, Plenum Press, New York. The practice of the present invention will employ, unless otherwise indicated, conventional methods of mass spectroscopy, protein chemistry, biochemistry, recombinant DNA techniques and pharmacology, within the skill of the art. The compositions and formulations described herein can be practiced employing the pharmaceutically acceptable excipients and salts available in *Remington's Pharmaceutical Sciences*, 18$^{th}$ Edition (Easton, Pa.: Mack Publishing Company, 1990).

"Compounds of the invention" refers to compounds encompassed by structural Formulae (I)-(V) disclosed herein. The compounds of the invention can be identified either by their chemical structure and/or chemical name. When the chemical structure and chemical name conflict, the chemical structures is determinative of the identity of the compound. The compounds of the invention may contain one or more chiral centers and/or double bonds and therefore, may exist as stereoisomers, such as double-bond isomers (i.e., geometric isomers), enantiomers or diastereoisomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention also include isotopically labeled compounds where one or more atoms have an atomic mass different from the atomic mass of conventionally found in nature. Examples of isotopes that may be incorporated into the compounds of the invention include, but are not limited to $^2$H, $^3$H, $^{13}$C, $^{15}$N, $^{18}$O, $^{17}$O, $^{31}$P, $^{32}$P, $^{35}$S, $^{18}$F and $^{36}$Cl. Further, it should be understood, when partial structures of the compounds of the invention are illustrated, that brackets of dashes indicate the point of attachment of the partial structure to the rest of the molecule.

"Composition of the invention" refers to at least one compound of the invention and a pharmaceutically acceptable vehicle, with which the compound is administered to a patient. When administered to a patient, the compounds of the invention are administered is isolated form, which means separated from a synthetic organic reaction mixture.

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1yl, cycloprop-2-en-1yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" specifically intended to include radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl," are used. Preferably, an alkyl group comprises from 1-20 carbon atoms, more preferably, from 1 to 10 carbon atoms.

"Alkanyl" refers to a saturated branched, straight-chain or cyclic alkyl radical derived by the removal of one hydrogen atom from a single carbon atom of a parent alkane. Typical alkanyl groups include but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl, cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien 1-yl, etc.; and the like.

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn3-yl, but-3-yn-1-yl, etc.; and the like.

"Acyl" refers to a radical —C(O)R, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to formyl, acetyl, cyclohexylcarbonyl, cyclohexylmethylcarbonyl, benzoyl, benzylcarbonyl and the like.

"Acyloxyalkyloxycarbonyl" refers to a radical —C(O)OCR'R"OC(O)R'", where R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —C(O)OCH$_2$OC(O)CH$_3$, —C(O)OCH$_2$OC(O)CH$_2$CH$_3$, —C(O)OCH(CH$_3$)OC(O)CH$_2$CH$_3$, —C(O)OCH(CH$_3$)OC(O)C$_6$H$_5$ and the like.

"Acylalkyloxycarbonyl" refers to a radical —C(O)OCR'R"C(O)R'", where R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —C(O)OCH$_2$C(O)CH$_3$, —C(O)OCH$_2$C(O)CH$_2$CH$_3$, —C(O)OCH(CH$_3$)C(O)CH$_2$CH$_3$, —C(O)OCH(CH$_3$)C(O)C$_6$H$_5$ and the like.

"Acyloxyalkyloxycarbonylamino" refers to a radical —NRC(O)OCR'R"OC(O)R'", where R, R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —NHC(O)OCH$_2$OC(O)

CH$_3$, —NHC(O)OCH$_2$OC(O)CH$_2$CH$_3$, —NHC(O)OCH(CH$_3$)OC(O)CH$_2$CH$_3$, —NHC(O)OCH(CH$_3$)OC(O)C$_6$H$_5$ and the like.

"Acylalkyloxycarbonylamino" refers to a radical —NRC(O)OCR'R"OC(O)R''', where R, R', R", and R''' are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —NHC(O)OCH$_2$C(O)CH$_3$, —NHC(O)OCH$_2$C(O)CH$_2$CH$_3$, —NHC(O)OCH(CH$_3$)C(O)CH$_2$CH$_3$, —NHC(O)OCH(CH$_3$)C(O)C$_6$H$_5$ and the like.

"Acylamino" refers to "Amide" as defined herein.

"Alkylamino" means a radical —NHR where R represents an alkyl, or cycloalkyl group as defined herein that may be optionally substituted by one or more substituents as defined herein. Representative examples include, but are not limited to, methylamino, ethylamino, 1-methylethylamino, cyclohexylamino and the like.

"Alkoxy" refers to a radical —OR where R represents an alkyl, or cycloalkyl group as defined herein that may be optionally substituted by one or more substituents as defined herein. Representative examples include, but are not limited to methoxy, ethoxy, propoxy, butoxy, cyclohexyloxy and the like.

"Alkoxycarbonyl" refers to a radical —C(O)-alkoxy where alkoxy is as defined herein.

"Alkoxycarbonylalkoxy" refers to a radical —OCR'R"OC(O)-alkoxy where alkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OCH$_3$, —OCH$_2$C(O)OCH$_2$CH$_3$, —OCH(CH$_3$)C(O)OCH$_2$CH$_3$, —OCH(C$_6$H$_5$)C(O)OCH$_2$CH$_3$, —OCH(CH$_2$C$_6$H$_5$)C(O)OCH$_2$CH$_3$, —OC(CH$_3$)(CH$_3$)C(O)OCH$_2$CH$_3$, and the like.

"Alkoxycarbonylalkylamino" refers to a radical —NRCR'R"C(O)-alkoxy where alkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OCH$_3$, —N(CH$_3$)CH$_2$C(O)OCH$_2$CH$_3$, —NHCH(CH$_3$)C(O)OCH$_2$CH$_3$, —NHCH(C$_6$H$_5$)C(O)OCH$_2$CH$_3$, —NHCH(CH$_2$C$_6$H$_5$)C(O)OCH$_2$CH$_3$, —NHC(CH$_3$)(CH$_3$)C(O)OCH$_2$CH$_3$, and the like.

"Alkylsulfonyl" refers to a radical —S(O)$_2$R where R is an alkyl, or cycloalkyl group as defined herein that may be optionally substituted by one or more substituents as defined herein. Representative examples include, but are not limited to, methylsulfonyl, ethylsulfonyl, propylsulfonyl, butylsulfonyl, and the like.

"Alkylsulfinyl" refers to a radical —S(O)R where R is an alkyl, or cycloalkyl group as defined herein that may be optionally substituted by one or more substituents as defined herein. Representative examples include, but are not limited to, methylsulfinyl, ethylsulfinyl, propylsulfinyl, butylsulfinyl, and the like.

"Alkylthio" refers to a radical —SR where R is an alkyl or cycloalkyl group as defined herein that may be optionally substituted by one or more substituents as defined herein. Representative examples include, but are not limited to methylthio, ethylthio, propylthio, butylthio, and the like.

"Amide or Acylamino" refers to a radical —NR'C(O)R", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, formylamino acetylamino, cyclohexylcarbonylamino, cyclohexylmethylcarbonyl-amino, benzoylamino, benzylcarbonylamino and the like.

"Amino" refers to the radical —NH$_2$

"Aryl" refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorine, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleidene, pyrene, pyranthrene, rubicene, triphenylene, trinaphthalene, and the like. Preferable, an aryl group comprises from 6 to 20 carbon atoms, more preferably, between 6 to 12 carbon atoms.

"Arylalkyl" refers to an acyclic alkyl in which one of the hydrogen atoms bonded to a carbon atom, typically a terminal or sp$^3$ carbon atom, is replaced with an aryl group. Typically arylalkyl groups include, but not limited to, benzyl, 2-phenylethan-1-yl, 2-phenylethen-1-yl, naphthylmethyl, 2-naphthylethan-1-yl, 2-naphthylethene-1-yl, naphthobenzyl, 2-naphthophenylethan-1-yl and the like. Where specific alkyl moieties are intended, the nomenclature arylalkany, arylalkenyl and/or arylalkynyl is used. Preferably, an arylalkyl group is (C$_6$-C$_{30}$)arylalkyl, e.g., the alkanyl, alkenyl or alkynyl moiety of the arylalkyl group is (C$_1$-C$_{10}$) and the aryl moiety is (C$_6$-C$_{20}$), more preferably, an arylalkyl group is (C$_6$-C$_{20}$) arylalkyl, e.g., the alkanyl, alkenyl or alkynyl moiety of the arylalkyl group is (C$_1$-C$_8$) and the aryl moiety is (C$_6$-C$_{12}$).

"Arylalkoxy" refers to an —O-arylalkyl radical where arylalkyl is as defined herein that may be optionally substituted by one or more substituents as defined herein.

"Arylalkoxycarbonylalkoxy" refers to a radical —OCR'R"C(O)-arylalkoxy where arylalkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OCH$_2$C$_6$H$_5$, —OCH(CH$_3$)C(O)OCH$_2$C$_6$H$_5$, —OCH(C$_6$H$_5$)C(O)OCH$_2$C$_6$H$_5$, —OCH(CH$_2$C$_6$H$_5$)C(O)OCH$_2$C$_6$H$_5$, —OC(CH$_3$)(CH$_3$)C(O)OCH$_2$C$_6$H$_5$, and the like.

"Arylalkoxycarbonylalkylamino" refers to a radical —NRCR'R"C(O)-arylalkoxy where arylalkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OCH$_2$C$_6$H$_5$, —N(CH$_3$)CH$_2$C(O)OCH$_2$C$_6$H$_5$, —NHCH(CH$_3$)C(O)OCH$_2$C$_6$H$_5$, —NHCH(C$_6$H$_5$)C(O)OCH$_2$C$_6$H$_5$, —NHCH(CH$_2$C$_6$H$_5$)C(O)OCH$_2$C$_6$H$_5$, —NHC(CH$_3$)(CH$_3$)C(O)OCH$_2$C$_6$H$_5$, and the like.

"Aryloxycarbonyl" refers to radical —C(O)—O-aryl where aryl is defined herein that may be optionally substituted by one or more substituents as defined herein.

"Aryloxycarbonylalkoxy" refers to a radical —OCR'R"C(O)-aryloxy where aryloxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OC$_6$H$_5$, —OCH(CH$_3$)C(O)OC$_6$H$_5$, —OCH(C$_6$H$_5$)C(O)OC$_6$H$_5$, —OCH(CH$_2$C$_6$H$_5$)C(O)OC$_6$H$_5$, —OC(CH$_3$)(CH$_3$)C(O)OC$_6$H$_5$, and the like.

"Aryloxycarbonylalkylamino" refers to a radical-NRCR'R"C(O)-aryloxy where aryloxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OC$_6$H$_5$, —N(CH$_3$)CH$_2$C(O)OC$_6$H$_5$, —NHCH(CH$_3$)C(O)OC$_6$H$_5$, —NHCH(C$_6$H$_5$)C(O)OC$_6$H$_5$, —NHCH(CH$_2$C$_6$H$_5$)C(O)OC$_6$H$_5$, —NHC(CH$_3$)(CH$_3$)C(O)OC$_6$H$_5$, and the like.

"Carbamoyl" refers to the radical —C(O)NRR where each R group is independently, hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Carbamate" refers to a radical —NR'C(O)OR", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methylcarbamate (—NHC(O)OCH$_3$), ethylcarbamate (—NHC(O)OCH$_2$CH$_3$), benzylcarbamate (—NHC(O)OCH$_2$C$_6$H$_5$), and the like.

"Carbonate" refers to a radical —OC(O)OR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methyl carbonate (—C(O)OCH$_3$), cyclohexyl carbonate (—C(O)OC$_6$H$_{11}$), phenyl carbonate (—C(O)OC$_6$H$_5$), benzyl carbonate (—C(O)OCH$_2$C$_6$H$_5$), and the like.

"Carboxy" means the radical —C(O)OH.

"Cyano" means the radical —CN.

"Cycloalkyl" refers to a substituted or unsubstituted cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In a preferred embodiment, the cycloalkyl group is (C$_3$-C$_{10}$) cycloalkyl, more preferably (C$_3$-C$_7$) cycloalkyl.

"Cycloheteroalkyl" refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Cycloheteroalkoxycarbonyl" refers to a radical —C(O)—OR where R is cycloheteroalkyl as defined herein that may be optionally substituted by one or more substituents as defined herein.

"Dialkylamino" means a radical —NRR' where R and R' independently represent an alkyl or cycloalkyl group as defined herein that may be optionally substituted by one or more substituents as defined herein. Representative examples include, but are not limited to dimethylamino, methylethylamino, di-(1-methylethyl)amino, (cyclohexyl)(methyl)amino, (cyclohexyl)(ethyl)amino, (cyclohexyl)(propyl)amino, and the like.

"Derived from a drug" refers to a fragment that is structurally related to such a drug. The structure of the fragment is identical to the drug except where a hydrogen atom attached to a heteroatom (N or O) has been replaced with a covalent bond to another group (typically, a promoiety). Note that when a drug is a salt form of a carboxylic, phosphonic or phosphoric acid, the corresponding structural fragment derived from such a drug is considered to be derived from the protonated acid form.

"Drug" refers to a compound that exhibits therapeutic and/or prophylactic and/or diagnostic utility when administered in effective amounts to a patient or a mammal.

"Ester" refers to a radical —C(O)OR, where R is alkyl, substituted alkyl, cycloalkyl, substituted cycloalkyl, cycloheteroalkyl, substituted cycloheteroalkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl as defined herein that may be optionally substituted by one or more substituents as defined herein. Representative examples include, but are not limited to, methyl ester (—C(O)OCH$_3$), cyclohexyl ester (—(O)OC$_6$H$_{11}$), phenyl ester (—C(O)OC$_6$H$_5$), benzyl ester (—C(O)OCH$_2$C$_6$H$_5$), and the like.

"Ether" refers to a radical —OR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Halo" means fluoro, chloro, bromo, or iodo.

"Heteroalkoxy" means an —O-heteroalkyl radical where heteroalkyl is as defined herein that may be optionally substituted by one or more substituents as defined herein.

"Heteroalkyl, Heteroalkanyl, Heteroalkenyl, Heteroalkynyl" refer to alkyl, alkanyl, alkenyl and alkynyl groups, respectively, in which one or more of the carbon atoms (and any associated hydrogen atoms) are each independently replaced with the same or different heteroatomic groups. Typical heteroatomic groups include, but are not limited to —O—, —S—, —O—O—, —S—S—, —OS—, —NR'—, =N—N=, —N=N—, —N=N—NR'—, —PH—, —P(O)$_2$—, —O—P(O)—, —S(O)—, —S(O)$_2$—, —SnH$_2$—, and the like, wherein R' is hydrogen, alkyl, substituted alkyl, cycloalkyl, substituted cycloalkyl, aryl or substituted aryl that may be optionally substituted by one or more substituents as defined herein.

"Heteroaryl" refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-20 membered heteroaryl, with 5-10 membered heteroaryl being particularly preferred. Preferred heteroaryl groups are those derived from thiophene, pyrrole, benzothiophene, benzofuran, indole, pyridine, quinoline, imidazole, oxazole and pyrazine.

"Heteroaryloxycarbonyl" refers to a radical —C(O)—OR where R is heteroaryl as defined that may be optionally substituted by one or more substituents as defined herein.

"Heteroarylalkyl" refers to an acyclic alkyl radical in which one of the hydrogen atoms bonded to a carbon atom, typically a terminal or sp3 carbon atom, is replaced with a heteroaryl group. Where specific alkyl moieties are intended, the nomenclature heteroarylalkanyl, heteroarylalkenyl and/or heteroarylalkynyl is used. Preferably, the heteroarylalkyl radical is a 6-30 carbon membered heteroarylalkyl, e.g., the alkanyl, alkenyl or alkynyl moiety of the heteroarylalkyl is 1-10 membered and the heteroaryl moiety is a 5-20 membered heteroaryl, more preferably, a 6-20 membered heteroarylalkyl, e.g., the alkanyl, alkenyl or alkynyl moiety of the heteroarylalkyl is 1-8 membered and the heteroaryl moiety is a 5-12 membered heteroaryl.

"Hydroxy" means the radical —OH.

"Oxo" means the divalent radical =O.

As used herein, the term "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

"Pharmaceutically acceptable" means approved or approvable by a regulatory agency of the Federal or state government or listed in the U.S. Pharmacopoeia or other generally recognized pharmacopoeia for use in animals, and more particularly in humans.

"Pharmaceutically acceptable salt" refers to a salt of a compound of the invention, which is pharmaceutically acceptable and possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentane propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tertiary butylacetic acid, laurylsulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Phosphate" refers to a radical —OP(O)(OR')(OR"), where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Phosphonate" refers to a radical —P(O)(OR')(OR"), where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Preventing" or "Prevention" refers to a reduction in risk of acquiring a disease or disorder (i.e., causing at least one of the clinical symptoms of the disease not to develop in a patient that may be exposed to or preposed to the disease but does not yet experience or display symptoms of the disease).

"Prodrug" refers to a derivative of a drug molecule that requires a transformation within the body to release the active drug. Prodrugs are frequently (though not necessarily) pharmacologically inactive until converted to the parent drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a group of atoms that when attached to a reactive group in a molecule masks, reduces or prevents that reactivity. Examples of protecting groups can be found in Green et al., "Protective Groups in Organic Chemistry", (Wiley, $2^{nd}$ ed. 1991) and Harrison et al., "Compendium of Synthetic Organic Methods", vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilylethanesulfonyl ("SES"), trityl and substituted trityl groups, allyloxycarbonyl, 9-fluorenylmethyloxycarbonyl ("FMOC"), nitroveratryloxycarbonyl ("NVOC") and the like. Representative hydroxyl protecting groups include, but are not limited to, those where the hydroxyl group is either acylated or alkylated such as benzyl, and trialkylsilyl ethers and allyl ethers.

"Racemate" refers to an equimolar mixture of enantiomers of a chiral molecule.

"Soft moiety" refers to a moiety that contain hydrolysable bonds that can be incorporated into compounds according to the invention include but not limited are amide (—NHC(O)—), ester (—C(O)O—), carbonate (—OC(O)O—), phosphate (—OP(O)O—), sulfate (—OS(O)(O)O—), urethane (—NHC(O)O—), glycoside or other bonds that can be cleaved by hydrolases. A glycoside moiety is formed by the conjugation of a sugar group through its anomeric carbon to another group via oxygen (as an O-glycosidic bond) or sulfur (as a S-glycosidic bond).

"Spacer" refers to an alkyl, aryl, arylalkyl, heteroalkyl and heteroaryl group which is optionally substituted by acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylsulfinyl, alkylsulfonyl, alkylthio, amino, alkylamino, arylalkylamino, dialkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, sulfonamide and/or, in case of alkyl, optionally interrupted by one or more of O, S and N($R^{51}$). $R^{51}$ can be H, lower alkyl, and substituted lower alkyl.

"Substituted" refers to a group in which one or more hydrogen atoms are each independently replaced with the same or different substituents(s). Typical substituents include, but are not limited to, —X, —$R^{54}$, —O⁻, =O, —O$R^{54}$, —S$R^{54}$, —S, =S, —N$R^{54}R^{55}$, =N$R^{54}$, —CX$_3$, —CF$_3$, —CN, —OCN, —SCN, —NO, —NO$_2$, =N$_2$, —N$_3$, —S(O)$_2$O⁻, —S(O)$_2$OH, —S(O)$_2$O$R^{54}$, —OS(O)$_2$O$^{31}$, —OS(O)$_2$$R^{54}$, —P(O)(O—)$_2$, —P(O)(O$R^{14}$)(O$^{31}$), —OP(O)(O$R^{54}$)(O$R^{55}$), —C(O)$R^{54}$, —C(S)$R^{54}$, —C(O)O$R^{54}$, —C(O)N$R^{54}R^{55}$, —C(O)O⁻, —C(S)O$R^{54}$, —N$R^{56}$C(O)N$R^{54}R^{55}$, —N$R^{56}$C(S)N$R^{54}R^{55}$, —N$R^{57}$C(N$R^{56}$)N$R^{54}R^{55}$, and —C(N$R^{56}$)N$R^{54}R^{55}$, where each X is independently a halogen; each $R^{54}$, $R^{55}$, $R^{56}$ and $R^{57}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —N$R^{58}R^{59}$, —C(O)$R^{58}$ or —S(O)$_2$$R^{58}$ or optionally $R^{58}$ and $R^{59}$ together with the atom to which they are both attached form a cycloheteroalkyl or substituted cycloheteroalkyl ring; and $R^{58}$ and $R^{59}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl.

"Sulfate" refers to a radical —OS(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonamide" refers to a radical —S(O)(O)NR'R", where R' and R" are independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein or optionally R' and R" together with the atom to which they are both attached form a cycloheteroalkyl or substituted cycloheteroalkyl ring. Representative examples include but not limited to azetidinyl, pyrrolidinyl, piperidinyl, morpholinyl, 4-(NR''')-piperazinyl or imidazolyl group wherein said group may be optionally substituted by one or more substituents as defined herein. R''' hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonate" refers to a radical —S(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Thio" means the radical —SH.

"Thioether" refers to a radical —SR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Treating" or "Treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and is severity and the age, weight, etc., of the patient to be treated, and can be determined by one of skill in the art without undue experimentation.

Reference now will be made in detail to preferred embodiments of the invention. While the invention will be described in conjunction with preferred embodiments, it will be understood that it is not intended to limit the invention to those preferred embodiments. To the contrary, it is intended to cover alternatives, modifications, and equivalents as may be included within the spirit and scope of the invention as defined by the appended claims.

Compounds of the Invention

The present invention provides indanone based acetylcholinesterase inhibitors comprising compounds of structural Formula (I):

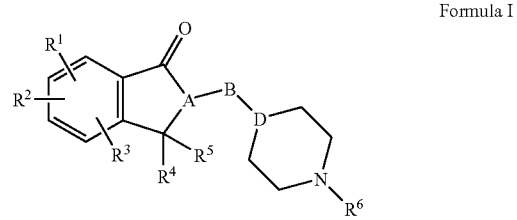

Formula I or a pharmaceutically acceptable salt, hydrate or solvate thereof provided that the compounds of the invention comprise a soft moiety conjugated directly or via a spacer onto or inserted into one of the substituents $R^1$, $R^2$, $R^3$, $R^4$, $R^5$ or $R^6$; wherein 'A' and 'D' are independently selected to be CH, or N;

'B' is selected to be —(CH$_2$)$_n$—, —(CH$_2$)$_n$C(O)—, —(CH$_2$)$_n$C(O)O—, —(CH$_2$)$_n$OC(O)—, —(CH$_2$)$_n$S(O)(O)—, —(CH$_2$)$_n$NHC(O)—, O, S, —C(O), —C(O)O, or —S(O)(O) wherein n=1-5;

$R^1$, $R^2$, $R^3$, $R^4$, $R^5$ and $R^6$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; preferably acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylsulfinyl, alkylsulfonyl, alkylthio, amino, alkylamino, arylalkylamino, dialkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, sulfonamide; optionally $R^1$ and $R^2$ or $R^2$ and $R^3$ together form 5- or 6-membered ring which may contain one or more heteroatoms selected from O, N, or S and that ring may be optionally substituted with substituents selected from alkyl, substituted alkyl, halo, hydroxyl, and carbonyl; optionally R⁴ and R⁵ together form 5- or 6-membered ring which may contain one or more heteroatoms selected from O, N, or S and that ring may be optionally substituted with substituents selected from alkyl, substituted alkyl, halo, hydroxyl, and carbonyl.

In one aspect of the invention, compounds of structural Formula (II) are described:

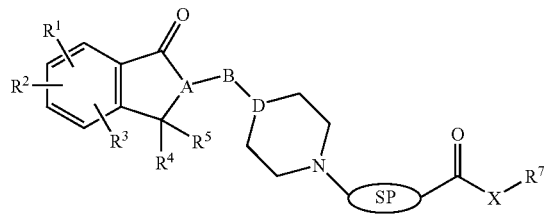

Formula II or a pharmaceutically acceptable salt, hydrate or solvate thereof; wherein X can be O, S, NH, or NR⁸;
SP is a spacer;
'A' and 'D' are independently selected to be CH, or N;
'B' is selected to be —(CH₂)ₙ—, —(CH₂)ₙC(O)—, —(CH₂)ₙC(O)O—, —(CH₂)ₙOC(O)—, —(CH₂)ₙS(O)(O)—, —(CH₂)ₙNHC(O)—, O, S, —C(O), —C(O)O, or —S(O)(O) wherein n is an interger between 1 and 5;
R¹, R², R³, R⁴, and R⁵ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonyl amino, acyloxyalkyloxycarbonyl amino, alkoxy, alkoxycarbonyl, alkoxycarbonylalkoxy, alkoxycarbonyllalkylamino, alkylsulfinyl, alkylsulfonyl, alkylthio, amino, alkylamino, arylalkylamino, dialkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally R¹ and R² or R² and R³ together form 5- or 6-membered ring which may contain one or more heteroatoms selected from O, N, or S and that ring may be optionally substituted with substituents selected from alkyl, substituted alkyl, halo, hydroxyl, and carbonyl; optionally R⁴ and R⁵ together form 5- or 6-membered ring which may contain one or more heteroatoms selected from O, N, or S and that ring may be optionally substituted with substituents selected from alkyl, substituted alkyl, halo, hydroxyl or carbonyl;
R⁷ is selected to be alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; R⁷ and R⁸ together form 5- or 6-membered ring which optionally may contain one or more heteroatoms selected from O, N, or S and that may be optionally substituted with one or more substituents selected from alkyl, halo, hydroxyl, carbonyl; or together with R⁸ forms 5- or 6-membered lactones and lactams that may be optionally substituted with one or more substituents selected from alkyl, halo, hydroxyl or carbonyl;

R⁸ is selected to be alkyl, substituted alkyl or R⁷ and R⁸ together form 5- or 6-membered ring which optionally may contain one or more heteroatoms selected from O, N, or S and that may be optionally substituted with one or more substituents selected from alkyl, halo, hydroxyl, carbonyl; or together with R⁷ forms 5- or 6-membered lactones and lactams that may be optionally substituted with one or more substituents selected from alkyl, halo, hydroxyl and carbonyl.

In another aspect of the invention, compounds comprise structural Formula (III):

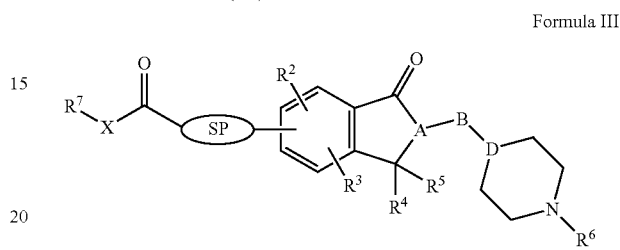

Formula III or a pharmaceutically acceptable salt, hydrate or solvate thereof; wherein X can be O, S, NH, or NR⁸;
SP can be a spacer;
'A' and 'D' are independently selected to be CH, or N;
'B' is selected to be —(CH₂)ₙ—, —(CH₂)ₙC(O)—, —(CH₂)ₙC(O)O—, —(CH₂)ₙOC(O)—, —(CH₂)ₙS(O)(O)—, —(CH₂)ₙNHC(O)—, O, S, —C(O), —C(O)O, or —S(O)(O) wherein n=1-5;
R², R³, R⁴, R⁵, and R⁶ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylsulfinyl, alkylsulfonyl, alkylthio, amino, alkylamino, arylalkylamino, dialkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, sulfonamide; optionally R² and R³ together form 5- or 6-membered ring which may contain one or more heteroatoms selected from O, N, or S and that ring may be optionally substituted with substituents selected from alkyl, substituted alkyl, halo, hydroxyl, carbonyl; optionally R⁴ and R⁵ together form 5- or 6-membered ring which may contain one or more heteroatoms selected from O, N, or S and that ring may be optionally substituted with substituents selected from alkyl, substituted alkyl, halo, hydroxyl or carbonyl;
R⁷ is selected to be alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; R⁷ and R⁸ together form 5- or 6-membered ring which optionally may contain one or more heteroatoms selected from O, N, or S and that may be optionally substituted with one or more substituents selected from alkyl, halo, hydroxyl, carbonyl; or together with R⁸ forms 5- or 6-membered lactones and lactams that may be optionally substituted with one or more substituents selected from alkyl, halo, hydroxyl or carbonyl;

R⁸ is selected to be alkyl, substituted alkyl or R⁷ and R⁸ together form 5- or 6-membered ring which optionally may contain one or more heteroatoms selected from O, N, or S and that may be optionally substituted with one or more substituents selected from alkyl, halo, hydroxyl, carbonyl; or together with R⁷ forms 5- or 6-membered lactones and lactams that may be optionally substituted with one or more substituents selected from alkyl, halo, hydroxyl and carbonyl.

In another aspect of the invention, compounds comprise structural Formula (IV):

Formula IV

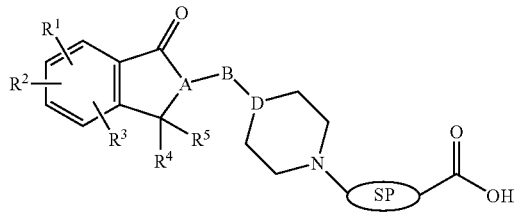

or a pharmaceutically acceptable salt, hydrate or solvate thereof; wherein X can be O, S, NH, or NR⁸;

SP can be a spacer;

'A' and 'D' are independently selected to be CH, or N;

'B' is selected to be —(CH₂)ₙ—, —(CH₂)ₙC(O)—, —(CH₂)ₙC(O)O—, —(CH₂)ₙOC(O)—, —(CH₂)ₙS(O)(O)—, —(CH₂)ₙNHC(O)—, O, S, —C(O), —C(O)O, or —S(O)(O) wherein n is an integer between 1 and 5;

R¹, R², R³, R⁴, and R⁵ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; preferably acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylsulfinyl, alkylsulfonyl, alkylthio, amino, alkylamino, arylalkylamino, dialkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, sulfonamide; optionally R¹ and R² or R² and R³ together form 5- or 6-membered ring which may contain one or more heteroatoms selected from O, N, or S and that ring may be optionally substituted with substituents selected from alkyl, substituted alkyl, halo, hydroxyl, carbonyl; optionally R⁴ and R⁵ together form 5- or 6-membered ring which may contain one or more heteroatoms selected from O, N, or S and that ring may be optionally substituted with substituents selected from alkyl, substituted alkyl, halo, hydroxyl and carbonyl.

In yet another aspect of the invention, compounds comprise structural Formula (V):

Formula V

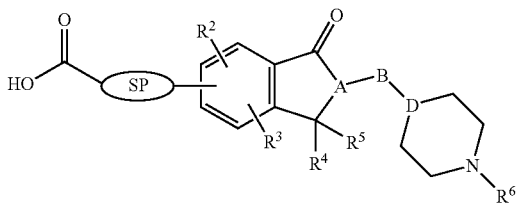

or a pharmaceutically acceptable salt, hydrate or solvate thereof; wherein X can be O, S, NH, or NR⁸;

SP can be a spacer;

'A' and 'D' are independently selected to be CH or N;

'B' is selected to be —(CH₂)ₙ—, —(CH₂)ₙC(O)—, —(CH₂)ₙC(O)O—, —(CH₂)ₙOC(O)—, —(CH₂)ₙS(O)(O)—, —(CH₂)ₙNHC(O)—, O, S, —C(O), —C(O)O, or —S(O)(O) wherein n=1-5;

R², R³, R⁴, R⁵, and R⁵ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; preferably acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylsulfinyl, alkylsulfonyl, alkylthio, amino, alkylamino, arylalkylamino, dialkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, sulfonamide; optionally R² and R³ together form 5- or 6-membered ring which may contain one or more heteroatoms selected from O, N, or S and that ring may be optionally substituted with substituents selected from alkyl, substituted alkyl, halo, hydroxyl, carbonyl; optionally R⁴ and R⁵ together form 5- or 6-membered ring which may contain one or more heteroatoms selected from O, N, or S and that ring may be optionally substituted with substituents selected from alkyl, substituted alkyl, halo, hydroxyl, and carbonyl.

The compounds of this invention described herein can have one or more of the following characteristics or properties:

(a) Compounds of the invention can have cholinesterase inhibitory activity;

(b) Compounds of the invention can have acetylcholinesterase inhibitory activity (c) Compounds of the invention can have butyrylcholinesterase inhibitory activity;

(d) Compounds according to the invention can contain at least one hydrolysable bond that can be cleaved non-oxidatively by hydrolytic enzyme(s);

(e) The primary metabolites of compounds result from a non-oxidative metabolic pathway;

(f) The primary metabolite(s), regardless of the electrophysiological properties of the parent drug, has, or can have, negligible inhibitory activity at the IKr (HERG) channel at the normal therapeutic concentration of the parent drug in plasma (e.g. the concentration of the metabolite must be at least five times higher than the normal therapeutic concentration of the parent compound before activity at the IKr channel is observed);

(g) Compounds of the invention, as well as the metabolites thereof, do not cause, or can have reduced incidence of metabolic drug-drug interaction (DDI) when co-administered with other drugs;

(h) Compounds of the invention, as well as metabolites thereof, do not substantially elevate liver function test (LFT) values when administered alone;

(i) Oral bioavailability of the compounds can be consistent with oral administration using standard pharmacological oral formulations; however, the compounds, and compositions thereof, can also be administered using any delivery system that produces constant and controllable blood levels overt time.

In one aspect, the invention provides compounds having any two or more of the above identified characteristics or properties. In another aspect, the invention provides for compounds having at least any three or more of the above identified properties or characteristics. In yet another aspect, the compounds, and compositions thereof, have any combination of four to seven of the above identified characteristics or properties. Preferably, the compounds of the invention have all nine characteristics or properties.

Preferably, the primary metabolite(s) of the inventive compounds, regardless of the electrophysiological properties of the parent drug, has, or have, negligible inhibitory activity at the iKr (HERG) channel at normal therapeutic concentrations of the drug in plasma. In other words, the concentration of the metabolite can be at least five times higher than the normal therapeutic concentration of the parent compound before activity at the IKr channel is observed. Preferably, the concentration of the metabolite can be at least ten times higher than the normal therapeutic concentration of the parent compound before activity at the IKr channel is observed.

Compounds according to the invention can be primarily metabolized by endogenous hydrolytic enzymes via hydrolysable bonds engineered into their structures. The primary metabolites resulting from this metabolic pathway are water soluble and do not have, or show a reduced incidence of, DDI when administered with other medications (drugs). Non-limiting examples of hydrolysable bonds that can be incorporated into compounds according to the invention include amide, ester, carbonate, phosphate, sulfate, urea, urethane, glycoside, or other bonds that can be cleaved by hydrolases.

Additional modifications of the compounds disclosed herein can readily be made by those skilled in the art. Thus, analogs and salts of the exemplified compounds are within the scope of the subject invention. With knowledge of the compounds of the subject invention skilled artisans can use known procedures to synthesize these compounds from available substrates. As used in this application, the term "analogs" refers to compounds which are substantially the same as another compound but which may have been modified by, for example, adding additional side groups. The term "analogs" as used in this application also may refer to compounds which are substantially the same as another compound but which have atomic or molecular substitution at certain locations in the compound.

The subject invention further pertains to enantiomerically isolated compounds, and compositions comprising the compounds. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. Thus, for example, the compounds are at least about 90% enantiomeric excess, preferably at least about 95% enantiomeric excess, more preferably at least about 97% enantiomeric excess, or even more preferably, at least 99% or greater than 99% enantiomeric excess.

Synthesis of the Compounds of the Invention

The compounds of the invention can be obtained via the synthetic methods illustrated in Schemes 1-12. Those of skill in the art will appreciate that a preferred synthetic route to the compounds of the invention will consist of attaching or incorporating soft-moieties to indanone derivatives of Formulae (I)-(V). Numerous methods have been described in the art for the synthesis of indanone analogs (see, e.g. Fillion, E. et al., *J. Org. Chem.* 2005, 70, 1316-1327; Sugimoto, H. et al., *J. Med. Chem.* 1995, 38, 4821-4829). Other methods are known in the art for synthesizing indanone, which are readily accessible to the skilled artisan. The soft-moieties attached to spacers thereof are commercially available or can be prepared by established procedures (See e.g., Green et al., "Protective Groups in Organic Chemistry," (Wiley, $4^{rd}$ ed., 2006); Harrison et al "Compendium of Synthetic Organic Methods," vols. 1-8 (John Wiley and Sons, 1971-1996); "Beilstein Handbook of Organic Chemistry, Frankfurt, Germany; Feiser et al, "Reagents for Organic Synthesis," Volumes 1-45, Karger, 1991; March, Advanced Organic Chemistry," Wiley Interscience, $4^{th}$ ed., 1991; Larock "Comprehensive Organic Transformations," Wiley-VCH Publishers, $2^{nd}$ ed., 1999; Paquette, "Encyclopedia of Reagents for Organic Synthesis," John Wiley and Sons, $1^{st}$ ed., 1995).

Accordingly, starting materials useful for preparing compounds of the invention and intermediates thereof are commercially available or can be prepared by well-known synthetic methods. Other methods for the synthesis of indanones described herein are either described in the art or will be readily apparent to the skilled artisan in view of the references provided above and may be used to synthesize the compounds of the invention. Accordingly, the methods presented in the Schemes herein are illustrative rather than comprehensive.

In one general method for synthesis of compounds of Formulae (I)-(V) is described in Scheme 1. An appropriate indanone (1) is used a starting building block. A number of substituted including functionalized indanones are commercially available from the well known vendors like Sigma-Aldrich, Acros, Alfa-Aesar. Many indanones comprising general structure (1) can also be prepared using literature methods (Premsagar et al. J. Org. Chem. 1981, 46, 2974-2976; Eaton et al. J. Org. Chem. 1973, 38, 4071-4073). A target indanone derivatives comprising structure (5) can be prepared from an appropriate indanone (1). A number methods have been developed in recent years to synthesize indanone derivatives of type (5) using indanones of type (1) (Sugimoto et al. J. Med. Chem. 1992, 35, 4542-4548; Sugimoto et al. U.S. Pat. Nos. 4,895,841 and 5,100,901; Pathi et al. WO 2007077443; Parthasaradhi et al. WO 2005003092; Dubey et al. WO 2005076749; Gutman et al. WO 200009483; Radhakrishnan et al. US 20040158070; Reddy et al. US 20040143121; limura et al. U.S. Pat. No. 6,252,081; Lensky, U.S. Pat. No. 5,606,064). In a typical reaction, an appropriate indanone (1) is condensed with a suitable 4-formylpiperidine (2) in the presence of a strong base like lithium diisopropylamide (LDA), potassium tert-butoxide or potassium hydroxide to give indanone (3) which after reduction using standard hydrogenation conditions gives the target indanone derivative (5). The standard hydrogenation conditions like hydrogen in the presence of platinum oxide, palladium-carbon, Raney nickel or ruthenium oxide catalyst can be used to transform (3) to (5). The formylpiperidine building block (2) can be prepared by following a reported method (Abe et al. Tetrahedron 2001, 57, 2701-2710; Miwa et al. Synlett 1994, 2, 109; Chen et al. EP 441517). The target indanone (5) can also be synthesized from indanone (1) by reacting with an appropriate piperidine (4) in the presence of a strong base like lithium diisopropylamide. The piperidine building blocks (4) can be prepared from isonipecotate using standard procedures well known in the art (Abe et al. Tetrahedron 2001, 57, 2701-2710).

Scheme 1

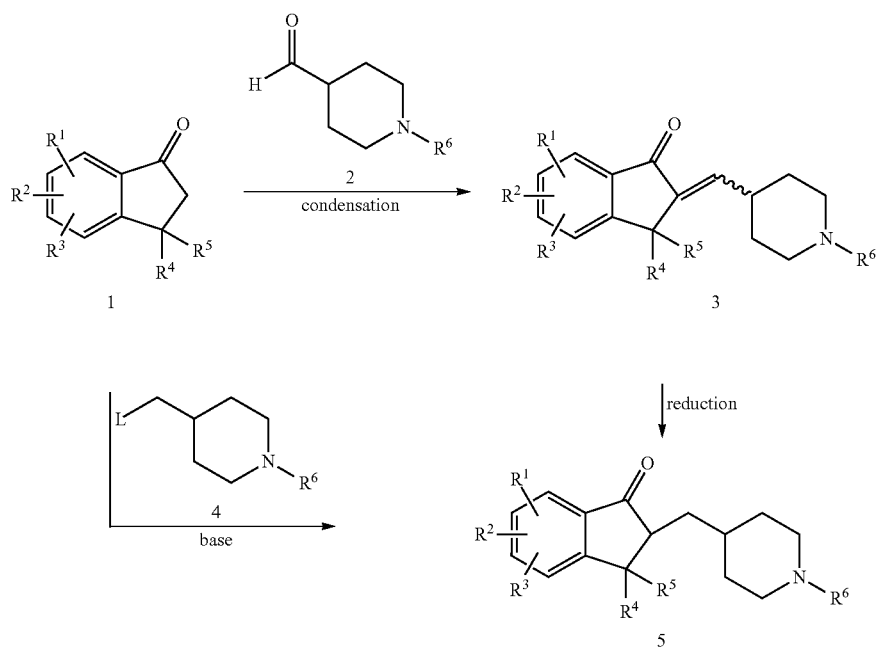

L = Leaving group like Cl, Br, I, O-tosyl, O-mesyl

Another general method for synthesis of compounds of Formulae (II) begins with an appropriate indanone (5) in a stepwise fashion as illustrated in Scheme 2. The indanone (5) can be derivatized with an appropriate spacer carrying a soft-moiety (8) under standard alkylating conditions well known in the art to provide the corresponding indanone derivative (7). The indanone derivative (5) having a suitable protecting group such as benzyl can be prepared from the compound (I) in a stepwise fashion as described for the synthesis compound (7) as illustrated in Scheme 1. The building blocks (8) can be prepared using standard procedures well known in the art. In a typical reaction, deprotection of N-benzyl group of compound (5) under standard hydrogenation conditions using palladium-carbon as catalyst gives the corresponding debenzylated indanone (6) which after reacting with a halo alkyl or benzyl derivative carrying a soft-moiety in presence of a mild base like diisopropylethylamine in a polar aprotic solvent like acetonitrile, DCM or DMF gives the target compound comprising the general structure (7).

Scheme 2

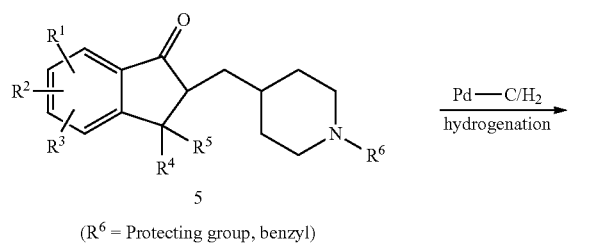

($R^6$ = Protecting group, benzyl)

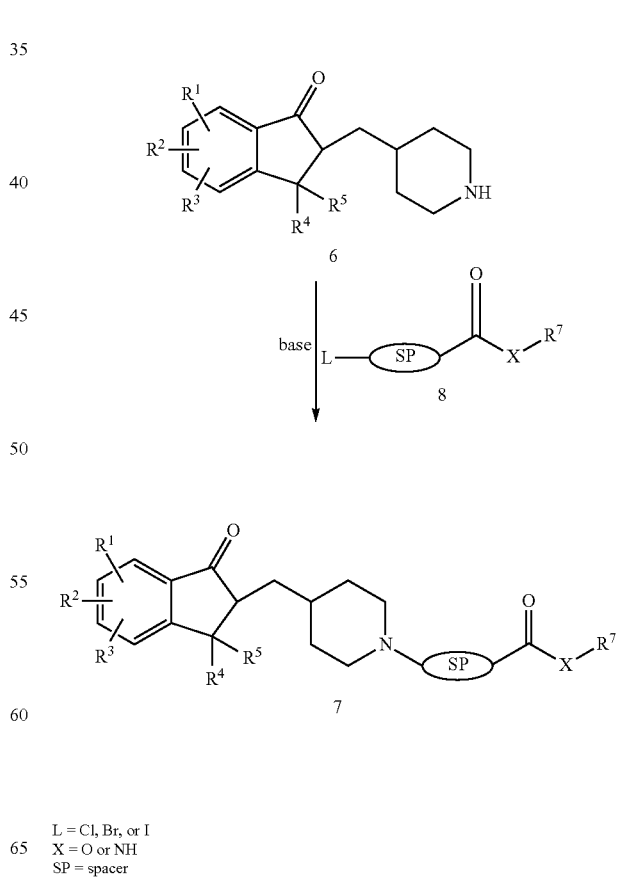

L = Cl, Br, or I
X = O or NH
SP = spacer

Scheme 3

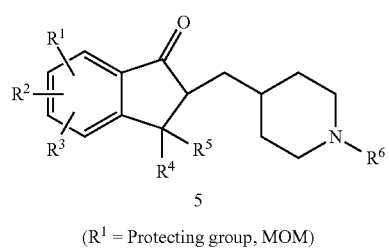

(R¹ = Protecting group, MOM)

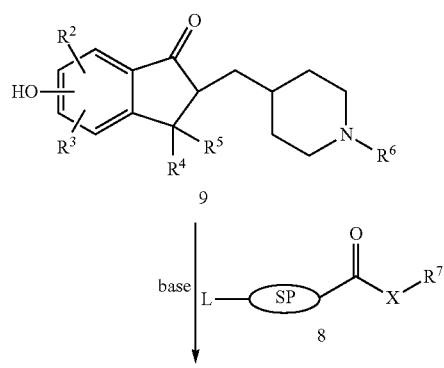

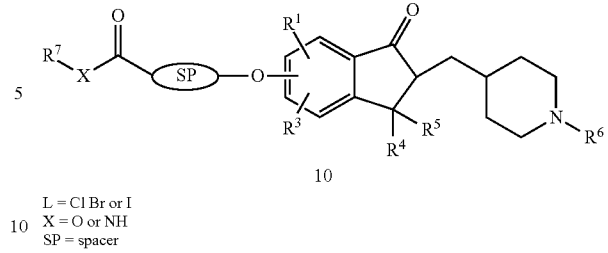

L = Cl Br or I
X = O or NH
SP = spacer

Another general method for synthesis of compounds of Formulae (III) is described in Scheme 3. The indanone (5) having a free phenolic hydroxyl group can be reacted with an appropriate spacer carrying a soft-moiety (8) under standard alkylating conditions well known in the art to provide the corresponding indanone derivative (10). The indanone derivative (5) having a free phenolic hydroxyl group can be prepared from the corresponding phenolic hydroxyl group protected indanone (5) with a suitable protecting group like MOM, TBS, BOC, PMB in a stepwise fashion as illustrated in Scheme 1. In a typical reaction, indanone (5) carrying a MOM protecting group under acidic conditions using trifluoroacetic acid (TFA) or hydrogen chloride (HCl) in a solvent like dichloromethane (DCM) gives the corresponding indanone (9) which after reacting with a halo alkyl or benzyl derivative carrying a soft-moiety in presence of a mild base like potassium carbonate or cesium carbonate in acetone or DMF provides the target compound comprising the general structure (10).

Scheme 4

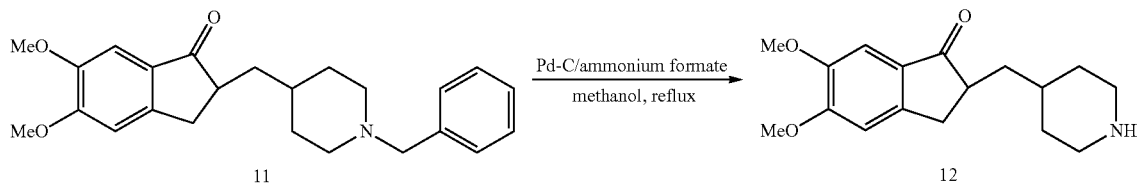

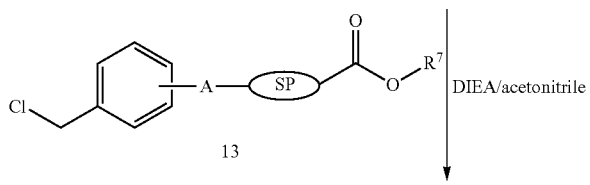

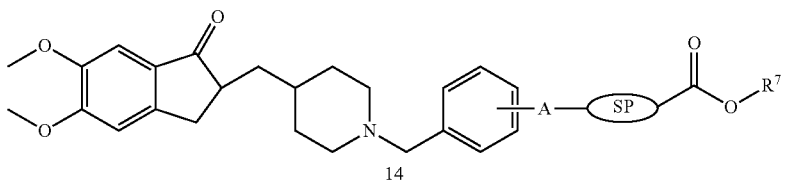

A = O, —C(O)O—, —C(O)NH, and OCH₂C(O)NH
SP = alkyl

In another general method the compounds of Formulae (IV) and (V) can be synthesized from the compounds comprising general Formulae (II) and (III) by hydrolyzing the terminal ester groups under standard conditions well known in the art.

In one method, selected indanone derivatives comprising Formula (II) were prepared as described in Scheme 4. The starting N-benzyl protected indanone derivative (11) was prepared using the reported methods as illustrated in Scheme 1. The benzyl group was deprotected by treating the compound (II) with palladium-carbon and ammonium formate in methanol at reflux temperature for two hours in nearly quantitative yield. The debenzylated indinone 12 was reacted with an appropriate benzyl chloride (13) carrying a soft-moiety in presence of a mild base DIEA at room temperature to 70° C. for 3 to 5 hours to give the target indanone derivative (14) in good yield. The building blocks benzylchlorides (13) were prepared as illustrated in Scheme 7 to 10.

Scheme 5

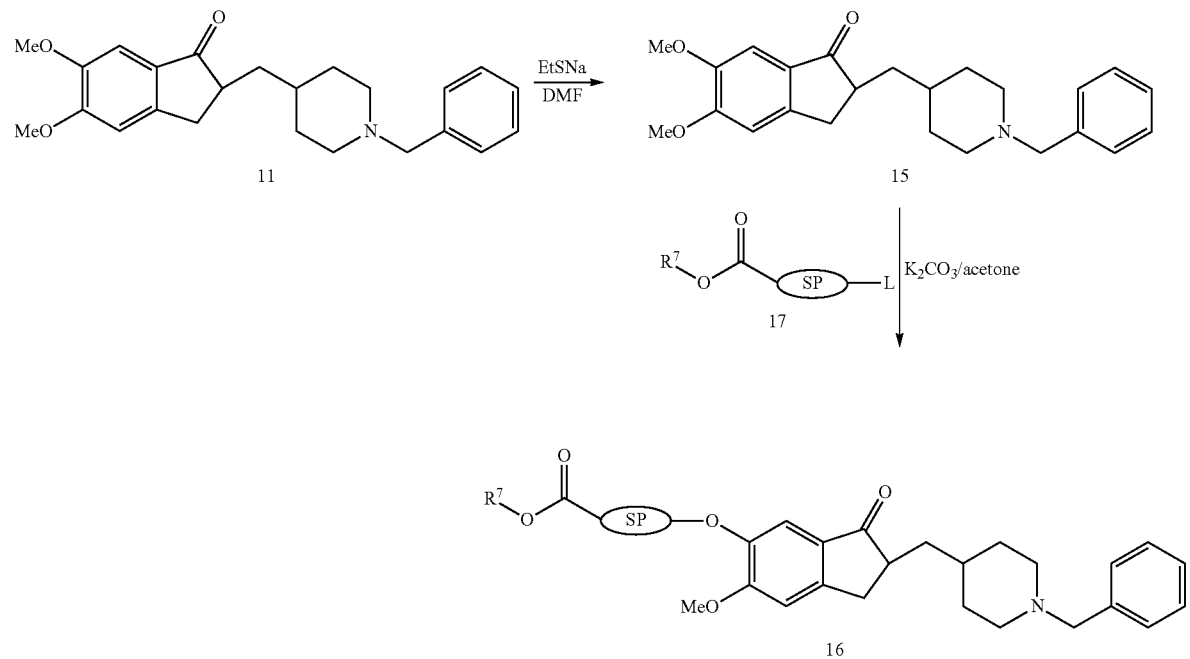

L = Br and Cl
R = ethyl tert-butyl
SP = —CH$_2$—, —CH$_2$CH$_2$CH$_2$—, —CH$_2$CH$_2$CH$_2$NHC(O)CH$_2$—

In another method selected indanone derivatives comprising Formula (III) were prepared as described in Scheme 5. The indanone (11) was treated with sodium ethanethiolate in DMF at around 70° C. to give corresponding indanone (15) in over 90% yield (Eur. J. Org. Chem. 2003, 9, 1681-1686). The indanone (15) was alkylated with an appropriate alkylhalide carrying terminal ester group (17) under standard conditions using potassium carbonate in acetone in good yields.

Scheme 6

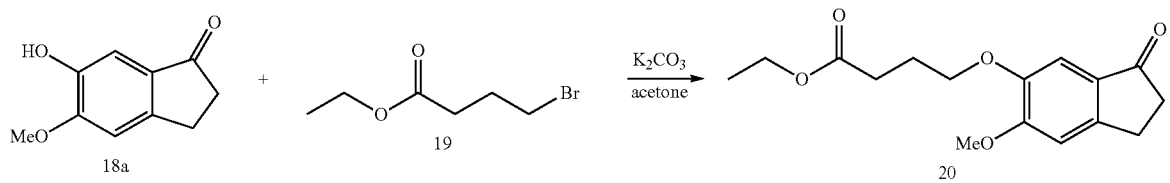

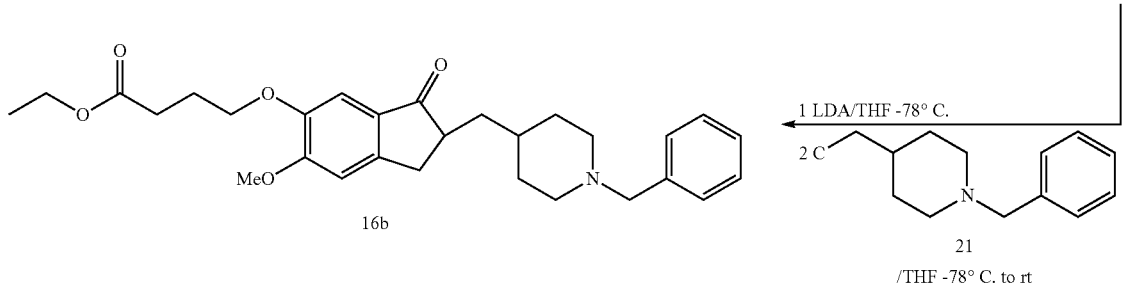

16b

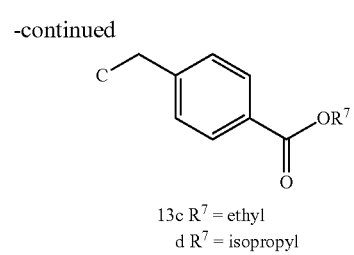

21

/THF -78° C. to rt

In another method selected indanone derivatives comprising Formula (III) were prepared as described in Scheme 6. The starting 6-hydroxy-5-methoxyindanone (18a) was prepared from vanillin (33a) in four steps as illustrated in Scheme 11. The indanone (18a) was reacted with ethyl 4-bromobutanoate (19) under standard alkylation conditions to give the corresponding indanone derivative (20) as described for the synthesis of indanone (16) as illustrated in Scheme 5. The indanone (20) was treated with chloromethylpiperidine (21) in presence of a strong base lithium diisopropylamide (LDA) in anhydrous THF at −78° C. to give the target indanone (16b).

The synthesis of building blocks carrying soft-moieties (13a-d) is described in Scheme 7. The chloromethyl substituted benzoic acids (23) and (24) were heated with ethanol at reflux temperature in presence of catalytic amounts of concentrated sulfuric acid for 5 to 8 hours to give the corresponding esters (13a) and (13c), respectively. Similarly, the chloromethyl substituted benzoates (13b) and (13d) were prepared under identical reaction conditions using isopropanol in nearly quantitative yields.

The building blocks (13e) (13f) and (13g) were prepared as described in Scheme 8. The chloromethyl substituted benzoic acid (23) was coupled with ethyl 4-aminobutanoate (26) using standard peptide coupling conditions to form the ester (13e). The 4-chloromethyl substituted benzoic acid derivatives (13f) and (13g) were also prepared under identical reaction conditions using ethyl 3-aminopropanoate (25) and the amino acid ester (26), respectively, in good yields.

The ester building blocks (13h and i) were prepared as described in Scheme 9. The phenols (27) were alkylated with appropriate bromoalkylcarboxylic acid esters (28) by heating in acetone in presence of a mild base potassium carbonate to give the corresponding esters (29) in good yields. The esters (29) were treated with thionyl chloride under standard reaction conditions to give the target ester building blocks (13h and 13i) in good yields.

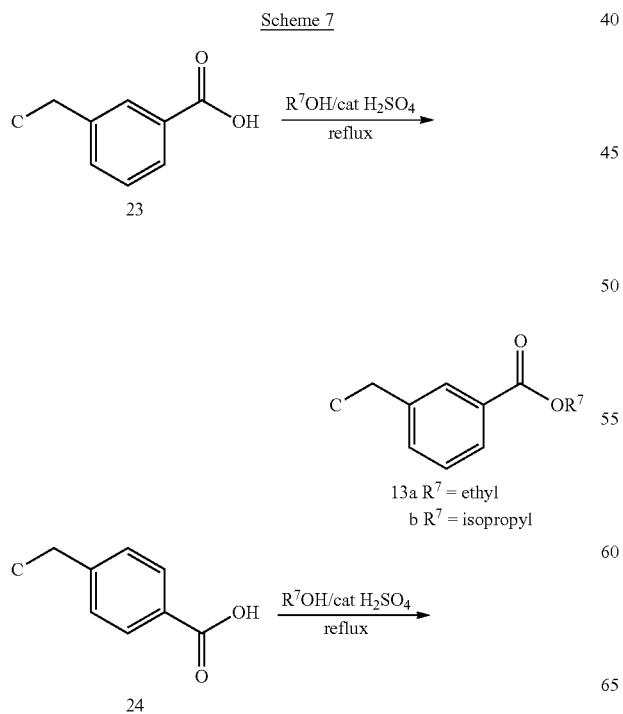

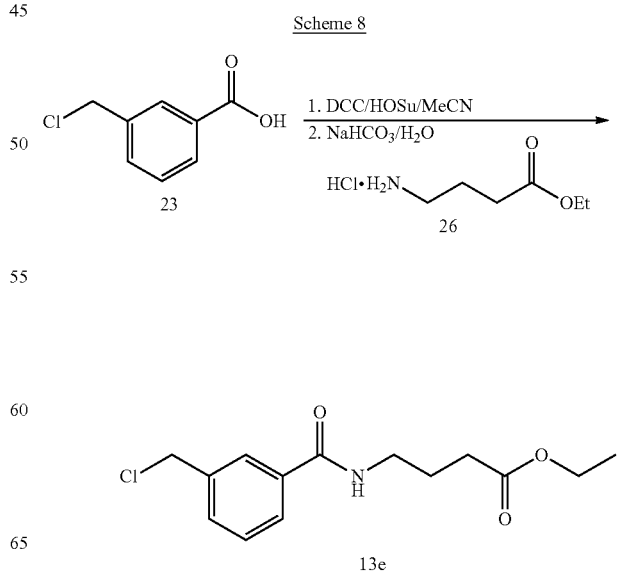

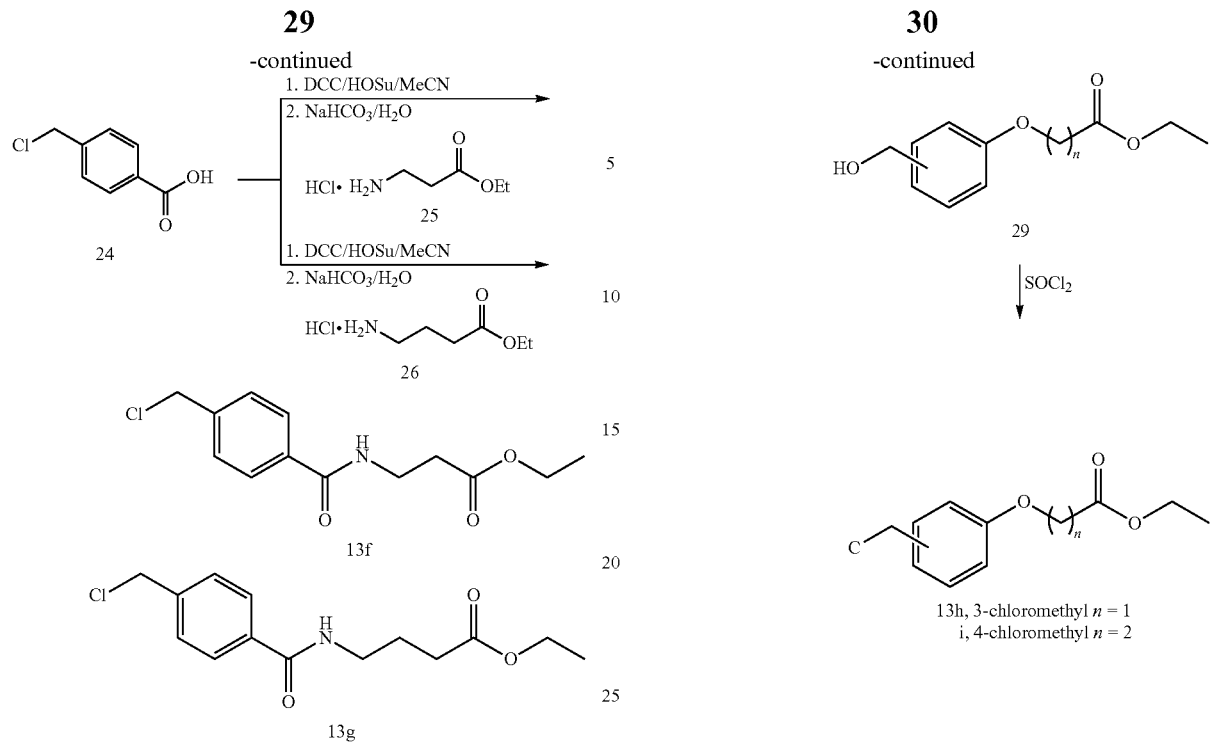

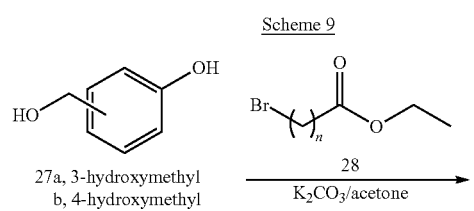

The ester building block (13j) was prepared in three steps as described in Scheme 10. The intermediate (31) was prepared in good yield by reacting ethyl ester of beta alanine (25) with chloroacetyl chloride (30) in presence of a mild base triethylamine (TEA) in DCM. The chloroalkylester (31) was coupled with phenol (27) under standard reaction conditions using mild base potassium carbonate in acetone at reflux temperature to give the compound 32 which after treating with thionyl chloride gave the target ester building block (13j) in overall good yield.

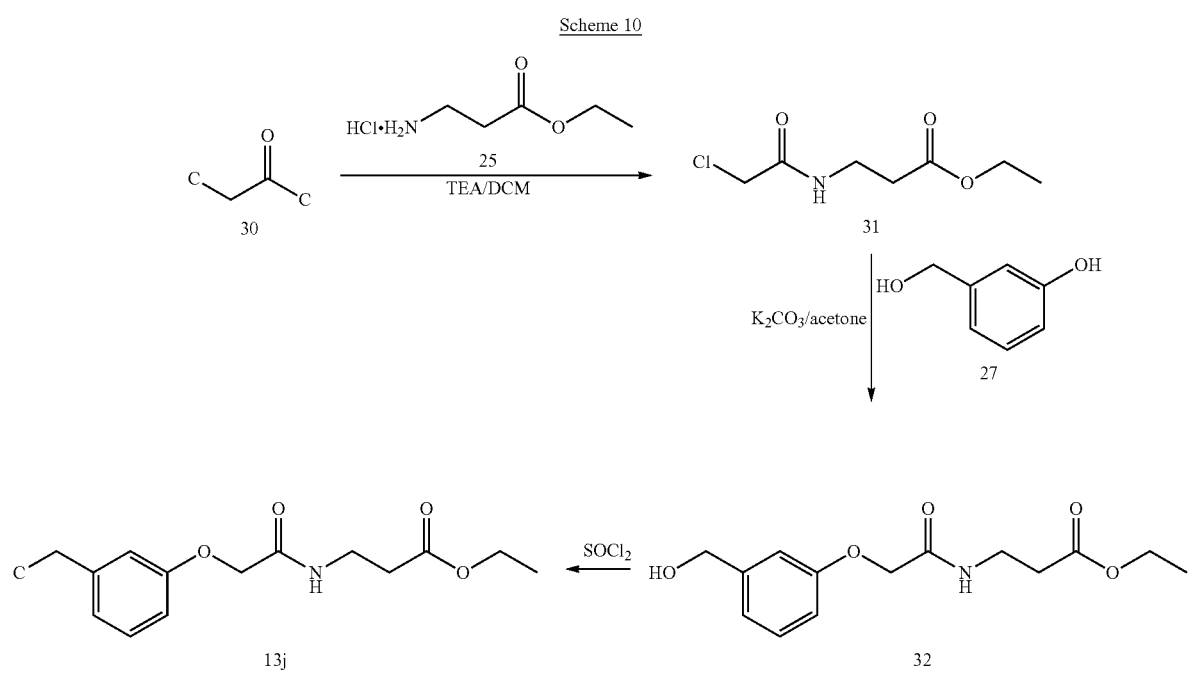

The indanone building blocks (18) were prepared as described in Scheme 11. The commercially available vanillin (33a) was reacted with Wittig reagent (34) in toluene at reflux temperature to give the corresponding unsaturated ester (35a) as cis and trans mixture. The ester (35a) was subjected to hydrogenation using palladium-carbon catalyst in methanol to give the saturated ester (36a). The ester (36a) was hydrolyzed using aqueous potassium hydroxide in THF to give carboxylic acid which after cyclization in the presence of concentrated sulfuric acid gave the target 6-hydroxyindan-1-one (18a) in overall good yield. Similarly, 5-hydroxyindan-1-one (18b) was prepared from the commercially available starting building block isovanilin (33b) in overall good yields.

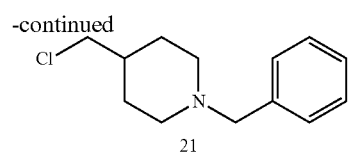

Therapeutic Uses of Compounds of Structural Formulae

The present invention provides methods of treating Alzheimer's disease. The present invention also provides methods for treatment and prevention of diseases such as Huntington's disease, Pick's disease, ataxia, myasthenia gravis and glaucoma.

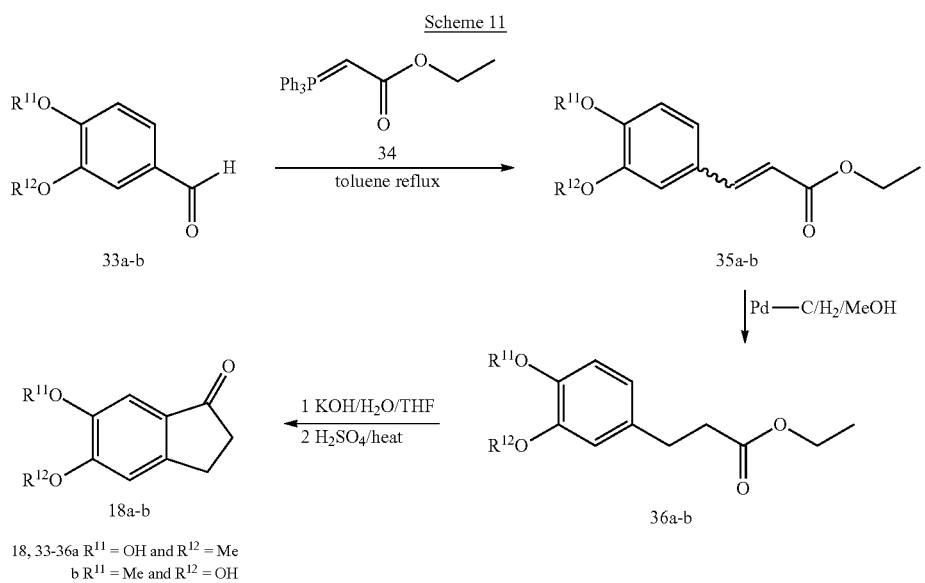

The N-benzyl substituted piperidine derivative (21) was prepared as described in Scheme 12. The commercially available 4-hydroxymethylpiperidine (38) was benzylated with benzyl bromide (39) using a mild base DIEA in acetonitrile to give the corresponding benzylated derivative (40)). The N-benzyl piperidine (40) was treated with thionyl chloride to give the target N-benzyl-4-chloromethylpiperidine (21) in overall good yield.

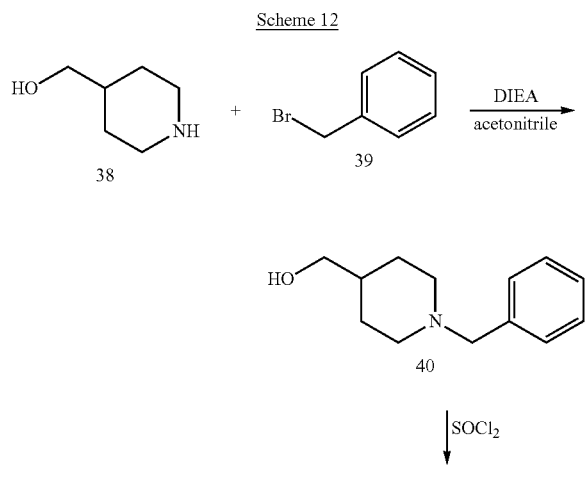

In accordance with the invention, a compound and/or a composition containing a compound of structural Formulae (I)-(V) can be administered to a patient, preferably a human, suffering from Alzheimer's disease. Further, in certain embodiments, the compounds and/or compositions of the invention can be administered to a patient, preferably a human, as a treatment or preventive measure against Huntington's disease, Pick's disease, ataxia, myasthenia gravis and glaucoma.

Thus, those of skill in the art may readily assay and use the compounds and/or compositions containing compound(s) of structural Formulae (I)-(V) to treat a medical condition for which inhibition of a cholinesterase is desired.

Therapeutic/Prophylactic Administration

The compounds, and/or compositions containing compounds(s), of structural Formulae (I)-(V) can be advantageously used in human medicine. As previously described in detail above, compounds and compositions containing compound(s) of structural Formulae (I)-(V) are useful for the treatment of Alzheimer's disease, Huntington's disease, Pick's disease, ataxia, myasthenia gravis and glaucoma.

When used to treat or prevent the above disease or disorders compounds and/or compositions of the invention can be administered or applied singly, in combination with other agents. The compounds and/or compositions of the invention can also be administered or applied singly or in combination with other pharmaceutically active agents, including other compounds and/or compositions of the invention.

The current invention provides methods for the treatment and/or prophylaxis by administration to a patient of a therapeutically effective amount of a composition and/or compound of the invention. The patient may be an animal, is more preferably a mammal, and most preferably a human.

The present compounds and/or compositions of the invention, which comprise one or more compounds and/or compositions of the invention are preferably administered orally. The compounds and/or compositions of the invention may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or composition of the invention. Methods of administration include, but are not limited to, intradermal, intramuscular, intraperitoneal, intravenous, subcutaneous, intranasal, epidural, oral, sublingual, intranasal, intracerebral, intravabinal, transdermal, rectally, by inhalation, or topically, particularly to the ears, nose, eyes or skin.

In particularly, preferred embodiments, the compounds and/or compositions of the invention can be delivered via sustained release systems, preferably oral sustained release systems. In one embodiment, a pump may be used (see, Langer, supra; Sefton, 1987, CRC Crit. Ref Biomed. Eng. 14:201; Saudek et al., 1989, N. Engl. J. Med. 321:574).

In another embodiment, polymeric materials can be used (see "Medical Applications of Controlled Release," Langer and Wise (eds.), Wiley, New York (1984); Ranger and Peppas, 1983, J. Macromol. Sci. Rev. Macromol Chem. 23:61; see also Levy et al., 1985, Science 228:190; During et al., 1989, Ann. Neurol. 25:351; Howard et al, 1989, J. Neurosurg. 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethers have been described in the art (Bamba et al., Int. J. Pharm., 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time controlled release), polymers that are degraded by enzymes (i.e., enzyme controlled release) and polymers that form firm layers that are destroyed by an increase in pressure (i.e., pressure-controlled release).

In still another embodiment, osmotic delivery systems are used for oral sustained release administration (Verma et al., Drug Dev. Ind. Pharm., 2000, 26:695-708). In a preferred embodiment, OROS® osmotic delivery systems sold by Alza Corporation of Mountain View, Calif. are used for oral sustained release delivery devices (See for example, Theeuwes et al., U.S. Pat. No. 3,845,770; and Theeuwes et al, U.S. Pat. No. 3,916,899).

In yet another embodiment, a controlled-release system can be placed in proximity of the target of the compounds and/or composition of the invention, thus requiring only a fraction of the systemic dose (See, e.g., Goodson, in "Medical Applications of Controlled Release," supra, vol. 2, pp. 115-138 (1984)). Other controlled-release systems discussed in Langer, 1990, Science 249:1527-1533 may also be used.

The compounds, and/or compositions containing compound(s) of structural Formulae (I)-(V) of the invention may be cleaved either chemically and/or enzymatically. One or more enzymes present in the stomach, intestinal lumen, intestinal tissue, blood, liver, brain or any other suitable tissue of a mammal may enzymatically cleave the compounds and/or compositions of the invention.

Compositions of the Invention

The present composition contain a therapeutically effective amount of one or more compounds of the invention, preferably in purified form, together with a suitable amount of a pharmaceutically acceptable vehicle, which so as to provide the form for proper administration to a patient. When administered to a patient, the compounds of the invention and pharmaceutically acceptable vehicles are preferably sterile. Water is preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present agents, or pH buffering agents. In addition, auxiliary, stabilizing, thickening, lubricating and coloring agents may be used.

Pharmaceutical compositions comprising a compound of the invention may be manufactured by means of conventional mixing, dissolving, granulating, dragee-making levigating, and emulsifying, encapsulating, entrapping or lyophilizing process. Pharmaceutical compositions may be formulated in conventional manner using one or more physiologically acceptable carriers, diluents, excipients or auxiliaries, which facilitate processing of compounds of the invention into preparations which can be used pharmaceutically. Proper formulation is dependent upon the route of administration chosen.

The present compositions can take the form of solutions, suspensions, emulsion, tablets, pills, pellets, and capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, $17^{th}$ Edition, 1985). Preferred compositions of the invention are formulated for oral delivery, particularly for oral sustained release administration.

Compositions for oral delivery may be in the form of tablets, lozenges, aqueous or oily suspensions, granules, powders, emulsions, capsules, syrups or elixirs, for example. Orally administered compositions may contain one or more optionally agents, for example, sweetening agents such as fructose, aspartame or saccharin; flavoring agents such as peppermint, oil of wintergreen, or cherry coloring agents and preserving agents to provide a pharmaceutically palatable preparation. Moreover, where in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about mM to about 50 mM) etc. Additionally, flavoring agents, preservatives, coloring agents, bile salts, acylcarnitines and the like may be added.

Compositions for administration via other routes may also be contemplated. For buccal administration, the compositions may take the form of tablets, lozenges, etc. formulated in conventional manner. Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as alcohol, glycol, polyglycol or fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611). A compound of the invention may also be formulated in rectal or vaginal compositions such as suppositories or retention enemas, e.g., containing conventional suppository bases such as cocoa, butter or other glycerides. In addition to the formulations described previously, a compound of the invention may also be formulated as depot preparation. Such long acting formulations may be administered by implantation (for example, subcutaneously or intramuscularly) or by intramuscular injection. Thus, for example, a compound of the invention may be formulated with suitable polymeric or hydrophobic materials (for example, as an emulsion in an acceptable oil) or ion exchange resins, or as sparingly soluble derivatives, for example, as a sparingly soluble salt.

When a compound of the invention is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

Methods of Use and Doses

A compound of the invention, or compositions thereof, will generally be used in an amount effective to achieve the intended purpose. For use to treat Alzheimer's disease, Huntington's disease, Pick's disease, ataxia, myasthenia gravis and glaucoma. The compounds of Formulae (I), (II), (III), (IV) or (V) and compositions containing a compound of Formulae (I), (II), (III), (IV) or (V) are administered or applied in a therapeutically effective amount.

The amount of a compound of the invention that will be effective in the treatment of a particular disorder or condition disclosed herein will depend on the nature of the disorder or condition, and can be determined by standard clinical techniques known in the art as previously described. In addition, in vitro or in vivo assays may optionally be employed to help identify optimal dosage ranges. The amount of a compound of the invention administered will, of course, is dependent on, among other factors, the subject being treated, and the weight of the subject, the severity of the affliction, the manner of administration and the judgment of the prescribing physician. For example, the dosage may be delivered in a pharmaceutical composition by a single administration, by multiple applications or controlled release. In a preferred embodiment, the compounds of the invention are delivered by oral sustained release administration. Preferably, in this embodiment, the compounds of the invention are administered twice per day (more preferably, once per day). Dosing may be repeated intermittently, may be provided alone or in combination with other drugs and may continue as long as required for effective treatment of the disease state or disorder.

The compounds and/or compositions containing compound(s), of structural Formulae (I)-(V) for the pharmacological treatment of Alzheimer's disease, Huntington's disease, Pick's disease, ataxia, myasthenia gravis and glaucoma may be administered in the range 0.1 mg to 500 mg preferably 1 mg to 100 mg per day given in one or more doses and more preferably 5 mg, 10 mg, 15 mg, 20 mg, 25 mg, 35 mg or 50 mg per day and most preferably 25 mg.

The compounds of the invention are preferably assayed in vitro and in vivo, for the desired therapeutic or prophylactic activity, prior to use in humans. The compounds of the invention may also be demonstrated to be effective and safe using animal model systems.

Preferably, the therapeutically effective dose of a compound of the invention described herein will provide therapeutic benefit without causing substantial toxicity. Toxicity of compounds of the invention may be determined using standard pharmaceutical procedures and may be readily ascertained by the skilled artisan. The dose ratio between toxic and therapeutic effect is the therapeutic index. A compound of the invention will preferably exhibit particularly high therapeutic indices in treating disease and disorders. The dosage of a compound of the inventions described herein will preferably be within a range of circulating concentrations that include an effective dose with little or no toxicity.

Combination Therapy

In certain embodiments of the present invention, the compounds of the invention can be used in combination therapy with at least one other therapeutic agent. The compound of the invention and the therapeutic agent can act additively or, more preferably, synergistically. In a preferred embodiment, composition comprising a compound of the invention is administered concurrently with the administration of another therapeutic agent, which can be part of the same composition. In another embodiment, a composition comprising a compound of the invention is administered prior or subsequent to administration of another therapeutic agent.

EXAMPLES

The invention is further defined by reference to the following examples, which describe in detail preparation of compounds and compositions of the invention and assays for using compounds and compositions of the invention. It will be apparent to those skilled in the art that many modifications, both to materials and methods, may be practiced without departing from the scope of the invention.

In the examples below, the following abbreviations have the following meanings. If an abbreviation is not defined, it has its generally accepted meaning.

AcOH=Acetic acid
Atm=Atmosphere
Cbz=carbobenzyloxy
DCM=dichloromethane
DMAP=4-N,N-dimethylaminopyridine
DMF=N,N-dimethylformamide
DMSO=dimethylsulfoxide
g=gram
h=hours
L=liter
LC/MS=liquid chromatography/mass spectroscopy
M=molar
mL=milliliter
mmol=millimols
nM=nanomolar
μM=micromolar
TBS=tert-butyldimethylsilyl
TEA=triethylamine
THF=tetrahydrofuran
TFA=trifluoroacetic acid Example 1

Synthesis of 5,6-dimethoxy-2-(piperidin-4-ylmethyl)-2,3-dihydro-1H-inden-1-one 12 (Scheme 4)

To a stirred suspension of palladium, 10 wt. % on activated carbon (4 g) in methanol (25 ml) at room temperature under nitrogen atmosphere was added a solution of indanone 11 (0.01 mol, 4.1 g) in methanol (25 ml) followed by ammonium formate (0.07 mol, 4.40 g). The resulting mixture was refluxed for 3 hours. The progress of the reaction was monitored by TLC. The reaction mixture was cooled to room temperature and filtered through a Celite® pad. The filtrate was concentrated on rotavapor and the residue was diluted with DCM (150 ml). The DCM solution was washed with water, dried over anhydrous sodium sulfate ($Na_2SO_4$) and evaporated the solvent. The residue was triturated with hexane to give the target indanone 12 as white solid in 97% yield (2.80 g).

$^1$H NMR (400 MHz, $CDCl_3$): δ 1.16-0.92 (3H, m); 1.58-1.40 (3H, m); 1.70-1.64 (1H, m); 2.51-2.39 (4H, m); 2.77 (1H, broad s); 2.92-2.87 (2H, m); 3.05-2.09 (1H, m); 3.67 (3H, s); 3.74 (3H, s); 6.66 (1H, s); 6.92 (1H, s). MS (ESI): m/z=290.20 (M+H$^+$).

Example 2

Ethyl 3-((4-((5,6-dimethoxy-1-oxo-2,3-dihydro-1H-inden-2-yl)methyl)piperidin-1-yl)methyl)benzoate 14a (Scheme 4)

To a stirred solution of indanone 12 (0.001 mol) and DIEA (0.002 mol) in anhydrous acetonitrile (10 ml) was added a solution of halide 13a (0.0012 mol) in anhydrous acetonitrile (2 ml) at room temperature. The resulting mixture was heated at 55-60° C. for 12 hours. The progress of the reaction was monitored by TLC. The reaction mixture was concentrated on rotavapor and the residue was diluted with ethyl acetate (50 ml). The resulting ethyl acetate solution was washed with water, dried over anhydrous sodium sulfate ($Na_2SO_4$) and evaporated the solvent. The residue was purified by silica gel column chromatography using a gradient of 0 to 100% ethyl acetate and hexane to get the title indanone 14a in 74% yield (0.33 g). $^1$H NMR (400 MHz, $CDCl_3$): δ 1.33-1.28 (3H, m); 1.37 (3H, t, J=7.2 Hz); 1.51-1.42 (1H, m); 1.73-1.62 (2H, m); 1.99-1.85 (3H, m); 2.69-2.65 (2H, m); 2.88-2.83 (2H, broad t); 3.24-3.17 (1H, m); 3.52 (2H, s); 3.88 (3H, s); 3.93 (3H, s); 4.35 (2H, q, J=7.2 Hz); 6.83 (1H, s); 7.14 (1H, s); 7.36 (1H, td, J=7.6, 2.4 Hz); 7.52 (1H, broad d); 7.91 (1H, dd, J=7.6, 1.2 Hz); 7.94 (1H, m). MS (ESI): m/z=452.30 (M+H$^+$).

Example 3

Isopropyl 3-((4-((5,6-dimethoxy-1-oxo-2,3-dihydro-1H-inden-2-yl)methyl)piperidin-1-yl)methyl)benzoate 14b was synthesized by reacting compounds 12 and 13b according to the procedure described for 14a in Example 2 (Scheme 4). The indanone 14b was isolated as colorless thick liquid in 81% (0.37 g) yield. $^1$H NMR (400 MHz, $CDCl_3$): δ 1.33-1.28 (3H, m); 1.35 (6H, d, J=6.4 Hz); 1.51-1.40 (1H, m); 1.72-1.62 (2H, m); 2.00-1.85 (3H, m); 2.68-2.65 (2H, m); 2.88-2.83 (2H, broad t); 3.23-3.17 (1H, m); 3.51 (2H, s); 3.87 (3H, s); 3.93 (3H, s); 5.22 (1H, quintet, J=6.0 Hz); 6.83 (1H, s); 7.14 (1H, s); 7.35 (1H, td, J=7.6, 2.4 Hz); 7.51 (1H, broad d); 7.89 (1H, dd, J=7.6, 1.2 Hz); 7.92 (1H, broad s). MS (ESI): m/z=466.30 (M+H$^+$).

Example 4

Ethyl 4-((4-((5,6-dimethoxy-1-oxo-2,3-dihydro-1H-inden-2-yl)methyl)piperidin-1-yl)methyl)benzoate 14c was synthesized by reacting compounds 12 and 13c according to the procedure described for 14a in Example 2 (Scheme 4). The indanone 14c was isolated as colorless thick liquid in 95% (0.42 g) yield. $^1$H NMR (400 MHz, $CDCl_3$): δ 1.35-1.27 (3H, m); 1.38 (3H, t, J=7.2 Hz); 1.54-1.42 (1H, m); 1.74-1.64 (2H, m); 2.01-1.87 (3H, m); 2.72-2.66 (2H, m); 2.88-2.83 (2H, broad t); 3.26-3.19 (1H, m); 3.53 (2H, s); 3.89 (3H, s); 3.95 (3H, s); 4.36 (2H, q, J=7.2 Hz); 6.84 (1H, s); 7.16 (1H, s); 7.38 (2H, d, J=8.4 Hz); 7.98 (2H, d, J=8.4 Hz). MS (ESI): m/z=452.30 (M+H$^+$). MS (ESI): m/z 452.20 (M+H$^+$).

Example 5

Isopropyl 4-((4-((5,6-dimethoxy-1-oxo-2,3-dihydro-1H-inden-2-yl)methyl)piperidin-1-yl)methyl)benzoate 14d was synthesized by reacting compounds 12 and 13d according to the procedure described for 14a in Example 2 (Scheme 4). The indanone 14d was isolated as colorless thick liquid in 73% (0.34 g) yield. $^1$H NMR (400 MHz, $CDCl_3$): δ 1.33-1.26 (3H, m); 1.35 (6H, d, J=6.4 Hz); 1.55-1.42 (1H, m); 1.74-1.64 (2H, m); 2.00-1.87 (3H, m); 2.72-2.66 (2H, m); 2.88-2.83 (2H, broad t); 3.25-3.19 (1H, m); 3.53 (2H, s); 3.89 (3H, s); 3.95 (3H, s); 5.24 (1H, quintet, J=6.4 Hz); 6.84 (1H, s); 7.16 (1H, s); 7.38 (2H, d, J=8.0 Hz); 7.97 (2H, d, J=8.0 Hz). MS (ESI): m/z=466.30 (M+H$^+$). MS (ESI): m/z=466.30 (M+H$^+$).

Example 6

Ethyl 4-(3-((4-((5,6-dimethoxy-1-oxo-2,3-dihydro-1H-inden-2-yl)methyl)piperidin-1-yl)methyl)benzamido)butanoate 14e was synthesized by reacting compounds 12 and 13e according to the procedure described for 14a in Example 2 (Scheme 4). The indanone 14e was isolated as colorless thick liquid in 80% (0.43 g) yield.

$^1$H NMR (400 MHz, $CDCl_3$): δ 1.23 (3H, t, J=7.2 Hz); 1.36-1.26 (3H, m); 1.55-1.42 (1H, m); 1.74-1.63 (2H, m); 1.98-1.86 (5H, m); 2.43 (2H, t, J=6.8 Hz); 2.71-2.65 (2H, m); 2.87-2.83 (2H, broad t); 3.25-3.19 (1H, m); 3.51-3.47 (2H, m); 3.52 (2H, s); 3.89 (3H, s); 3.94 (3H, s); 4.11 (2H, q, J=7.2 Hz); 6.56 (1H, broad triplet), 6.84 (1H, s); 7.15 (1H, s); 7.37 (2H, d, J=8.4 Hz); 7.72 (2H, d, J=8.4 Hz). MS (ESI): m/z=537.40 (M+H$^+$).

Example 7

Ethyl 3-(4-((4-((5,6-dimethoxy-1-oxo-2,3-dihydro-1H-inden-2-yl)methyl)piperidin-1-yl)methyl)benzamido)propanoate 14f was synthesized by reacting compounds 12 and 13f according to the procedure described for 14a in Example 2 (Scheme 4). The indanone 14f was isolated as colorless thick liquid in 82% (0.42 g) yield.

$^1$H NMR (400 MHz, CDCl$_3$): δ 1.27 (3H, t, J=7.2 Hz); 1.40-1.31 (3H, m); 1.55-1.42 (1H, m); 1.74-1.63 (2H, m); 2.00-1.87 (3H, m); 2.71-2.63 (4H, m); 2.89-2.84 (2H, broad t); 3.26-3.19 (1H, m); 3.52 (2H, s); 3.89 (3H, s); 3.95 (3H, s); 4.17 (2H, q, J=7.2 Hz); 6.84 (1H, s); 7.15 (1H, s); 7.36 (2H, t, J=7.6 Hz); 7.46 (1H, d, J=7.6 Hz); 7.63 (1H, d, J=7.6 Hz); 7.70 (1H, broad s). MS (ESI): m/z=523.40 (M+H$^+$).

Example 8

Ethyl 4-(4-((4-((5,6-dimethoxy-1-oxo-2,3-dihydro-1H-inden-2-yl)methyl)piperidin-1-yl)methyl)benzamido)butanoate 14g was synthesized by reacting compounds 12 and 13g according to the procedure described for 14a in Example 2 (Scheme 4). The indanone 14g was isolated as colorless thick liquid in 65%% (0.34 g) yield. $^1$H $^1$H NMR (400 MHz, CDCl$_3$): δ 1.23 (3H, t, J=7.2 Hz); 1.40-1.27 (3H, m); 1.55-1.42 (1H, m); 1.74-1.64 (2H, m); 1.92-1.83 (3H, m); 1.96 (2H, t, J=6.8 Hz), 2.43 (2H, t, J=7.2 Hz); 2.71-2.67 (2H, m); 2.89-2.84 (2H, broad t); 3.26-3.19 (1H, m); 3.51 (2H, q, J=6.8 Hz); 3.53 (2H, s); 3.90 (3H, s); 3.95 (3H, s); 4.12 (2H, q, J=6.8 Hz); 6.53 (1H, broad s); 6.85 (1H, s); 7.16 (1H, s); 7.38 (2H, d, J=8.4 Hz); 7.72 (2H, d, J=8.4 Hz). MS (ESI): m/z=537.40 (M+H$^+$).

Example 9

Ethyl 2-(3-((4-((5,6-dimethoxy-1-oxo-2,3-dihydro-1H-inden-2-yl)methyl)piperidin-1-yl)methyl)phenoxy)acetate 14h was synthesized by reacting compounds 12 and 13h according to the procedure described for 14a in Example 2 (Scheme 4). The indanone 14h was isolated as colorless thick liquid in 71% (0.34 g) yield. $^1$H NMR (400 MHz, CDCl$_3$): δ 1.21 (3H, t, J=7.2 Hz); 1.40-1.25 (4H, m); 1.66-1.55 (2H, m); 1.90-1.79 (3H, m); 2.63-2.59 (2H, m); 2.86-2.77 (2H, m); 3.19-3.14 (1H, m); 3.38 (2H, s); 3.81 (3H, s); 3.87 (3H, s); 4.18 (2H, q, J=7.2 Hz); 4.53 (2H, s); 6.71-6.68 (1H, m); 6.78 (s, 1H); 6.86-6.83 (2H, m); 7.07 (1H, s) 7.13 (1H, t, J=8.4 Hz). MS (ESI): m/z=482.30 (M+H$^+$).

Example 10

Ethyl 4-(4-((4-((5,6-dimethoxy-1-oxo-2,3-dihydro-1H-inden-2-yl)methyl)piperidin-1-yl)methyl)phenoxy)butanoate 14i was synthesized by reacting compounds 12 and 13i according to the procedure described for 14a in Example 2 (Scheme 4). The indanone 14i was isolated as colorless thick liquid in 32% (0.16 g) yield. $^1$H NMR (400 MHz, CDCl$_3$): δ 1.25 (3H, t, J=7.2 Hz); 1.38-1.27 (3H, m); 1.55-1.40 (1H, m); 1.73-1.63 (2H, m); 1.95-1.86 (3H, m); 2.09 (2H, quintet, J=7.6 Hz); 2.50 (2H, t, J=7.6 Hz); 2.71-2.65 (2H, m); 2.89-2.85 (2H, m); 3.25-3.18 (1H, m); 3.42 (2H, s); 3.89 (3H, s); 3.95 (3H, s); 3.98 (2H, t, J=6.0 Hz); 4.13 (2H, q, J=7.2 Hz); 6.82 (2H, d, J=8.4 Hz); 6.84 (1H, s); 7.15 (1H, s); 7.20 (2H, d, J=8.4 Hz). MS (ESI): m/z=510.30 (M+H$^+$).

Example 11

Ethyl 3-(2-(3-((4-((5,6-dimethoxy-1-oxo-2,3-dihydro-1H-inden-2-yl)methyl)piperidin-1-yl)methyl)phenoxy)acetamido)propanoate 14j was synthesized by reacting compounds 12 and 13j according to the procedure described for 14a in Example 2 (Scheme 4). The indanone 14j was isolated as colorless thick liquid in 40% (0.22 g) yield. $^1$H NMR (400 MHz, CDCl$_3$): δ 1.23 (3H, t, J=7.2 Hz); 1.36-1.26 (3H, m); 1.55-1.42 (1H, m); 1.74-1.63 (2H, m); 1.98-1.86 (3H, m); 2.43 (2H, t, J=6.8 Hz); 2.71-2.65 (2H, m); 2.87-2.83 (2H, broad t); 3.25-3.19 (1H, m); 3.51-3.47 (2H, m); 3.51 (2H, q, J=6.8 Hz); 3.89 (3H, s); 3.94 (3H, s); 4.11 (2H, q, J=7.2 Hz); 4.43 (2H, s); 6.71-6.68 (1H, m); 6.78 (1H, s); 6.86-6.83 (2H, m); 7.07 (1H, s) 7.13 (1H, t, J=8.4 Hz). MS (ESI): m/z=553.40 (M+H$^+$).

Example 12

2-((1-benzylpiperidin-4-yl)methyl)-6-hydroxy-5-methoxy-2,3-dihydro-1H-inden-1-one (Scheme 5)

A solution of indanone 11 (0.005 mol, 1.90 g) and sodium ethanethiolate (0.025 mol, 2.10 g) in anhydrous DMF (20 ml) was heated at 60° C. for 5 hours. The progress of the reaction was monitored by TLC. The reaction mixture was cooled to room temperature and poured in to ice cold water (100 ml). The resulting mixture was extracted with ethyl acetate (50 ml) and the aqueous layer was neutralized with 0.5N HCl (up to pH=approximately 7). Then the precipitate was filtered, washed with water (15 ml×3) and dried under vacuum to give the title indanone 15 as white solid in 43% yield (0.80 g). $^1$H NMR (400 MHz, CDCl$_3$): δ 1.40-1.31 (3H, m); 1.55-1.42 (1H, m); 1.74-1.63 (2H, m); 2.00-1.86 (3H, m); 2.70-2.63 (2H, m); 2.92-2.87 (2H, m); 3.22-3.16 (1H, m); 3.50 (2H, s); 3.91 (3H, s); 4.80 (1H, broad s); 6.90 (1H, s); 7.17 (1H, s); 7.25 (1H, m); 7.31-7.30 (4H, m). MS (ESI): m/z=366.20 (M+H$^+$).

Example 13 tert-Butyl 2-(2-((1-benzylpiperidin-4-yl)methyl)-6-methoxy-3-oxo-2,3-dihydro-1H-inden-5-yloxy)acetate 16a (Scheme 5)

To a stirred solution of indanone 15 (0.001 mol) in acetone (20 ml) was added anhydrous potassium carbonate (0.002 mol, 0.27 g) followed by tert-butyl bromoacetate 17a (0.0015 mol, 0.29 g). The resulting mixture was refluxed for 5 to 8 hours. The progress of the reaction was monitored by TLC. The reaction mixture was cooled to room temperature and filtered. The precipitate was washed with acetone (15 ml×2) and the combined filtrate was concentrated on rotavapor. The residue was diluted with ethyl acetate (50 ml), washed with water (25 ml×2), dried over anhydrous sodium sulfate (Na$_2$SO$_4$) and evaporated the solvent. The crude product was purified by silica gel column chromatography using 0-100% gradient of ethyl acetate and hexane to give the pure target indanone 16a as colorless thick liquid in 81% (0.38 g). $^1$H NMR (400 MHz, CDCl$_3$): δ 1.37-1.19 (3H, m); 1.45 (9H, s); 1.70-1.60 (2H, m); 1.95-1.84 (3H, m); 2.67-2.59 (3H, m); 2.87-2.84 (2H, m); 3.17-3.07 (1H, m); 3.46 (2H, s); 3.86 (3H, s); 4.62 (2H, s); 6.68 (1H, m); 7.15-7.14 (1H, m); 7.24-7.19 (1H, m); 7.28-7.24 (4H, m). MS (ESI): m/z=480.30 (M+H$^+$). MS (ESI): m/z=480.30 (M+H$^+$).

Example 14

Ethyl 4-(2-((1-benzylpiperidin-4-yl)methyl)-6-methoxy-3-oxo-2,3-dihydro-1H-inden-5-yloxy)butanoate 16b was synthesized by reacting compound 15 and ethyl 4-bromobutyrate 17b according to the procedure described for 16a in Example 13 (Scheme 5). The indanone 16b was isolated as white solid in 95% (0.44 g) yield. $^1$H NMR (400 MHz, CDCl$_3$): δ 1.25 (3H, t, J=7.2 Hz); 1.37-1.28 (3H, m); 1.55-1.42 (1H, m); 1.80-1.60 (2H, m); 1.96-1.92 (3H, m); 2.19 (2H, quintet, J=6.8 Hz); 2.54 (2H, t, J=7.2 Hz); 2.67-2.64 (2H, m); 2.91-2.86 (2H, m); 3.23-3.17 (1H, m); 3.49 (2H, s); 3.87 (3H, s); 4.17-4.11 (4H, m); 6.84 (1H, s); 7.15 (1H, s); 7.25-7.20 (1H, m); 7.31-7.30 (4H, m). MS (ESI): m/z=480.30 (M+H$^+$). MS (ESI): m/z=480.30 (M+H$^+$).

The Indanone 16b was also prepared by alkylating the indanone derivative 20 with N-benzyl substituted piperidine chloride 21 using LDA (Scheme 6). To a stirred solution of LDA (0.005 mol) in anhydrous THF (20 ml) at −78° C. under nitrogen atmosphere was added dropwise a solution of halide 21 (0.005 mol, 1.10 g) in THF (5 ml). The resulting mixture was stirred at −78 C for 2 h and then slowly warmed the reaction mixture to 0 C. The reaction was quenched with saturated ammonium chloride solution (50 ml). The resulting mixture was extracted with ethyl acetate, washed with water, dried over sodium sulfate and evaporated the solvent. The residue was purified by silica gel column chromatography using 0-100% gradient of ethyl acetate and hexane to give the pure indanone 16b in 21% yield. The $^1$H NMR and mass spectral data of the indanone 16b synthesized by this method (Scheme 6) is identical to the indanone 16b prepared using the method as illustrated in Scheme 5.

Example 15

Ethyl 3-(2-(2-((1-benzylpiperidin-4-yl)methyl)-6-methoxy-3-oxo-2,3-dihydro-1H-inden-5-yloxy)acetamido)propanoate 16c was synthesized by reacting compound 15 and ethyl 4-bromobutyrate 31 according to the procedure described for 16a in Example 13 (Scheme 5). The indanone 16c was isolated as colorless thick liquid in 65% yield (0.33 g). MS (ESI): m/z=523.30 (M+H$^+$).

Example 16

Ethyl 4-(6-methoxy-3-oxo-2,3-dihydro-1H-inden-5-yloxy)butanoate 20 (Scheme 6)

To a stirred solution of 6-hydroxy-5-methoxy-2,3-dihydro-1H-inden-1-one 18a (0.01 mol, 1.78 g) in acetone (50 ml) was added potassium carbonate (0.02 mol, 2.80 g). The resulting mixture was refluxed for 2 hours. After cooling to room temperature ethyl 4-bromobutyrate was added. The reaction mixture was stirred at 60° C. for 12 h. The progress of the reaction was monitored by TLC. The reaction mixture was filtered and the precipitate was washed with acetone (15 ml×2). The combined filtrate was concentrated on rotavapor and the residue was diluted with ethyl acetate. The ethyl acetate solution was successively washed with water, saturated sodium bicarbonate (Na$_2$HCO$_3$), water and dried over magnesium sulfate (Mg$_2$SO$_4$). After evaporation of the solvent the crude product was purified by passing through a short silica gel column using 0-50% gradient of ethyl acetate and hexane as eluent to give the pure indanone 20 as colorless thick liquid in 30% yield (0.87 g). $^1$H NMR (400 MHz, CDCl$_3$): δ 1.21 (3H, broad t); 2.16 (2H, m); 2.44 (2H, m); 2.59 (2H, m); 2.96 (2H, m); 3.93 (3H, s); 4.04 (2H, broad t); 4.10 (2H, broad q); 6.84 (1H, m); 7.43 (1H, s); 7.12 (1H, s). MS (ESI): m/z=293.20 (M+H$^+$).

Example 17

Ethyl 3-(chloromethyl)benzoate 13a (Scheme 7)

To a stirred solution of 3-(chloromethyl)benzoic acid 23 (0.01 mol, 1.70 g) in anhydrous ethanol (20 ml) was added few drops (approximately 0.2 ml) concentrated sulfuric acid was added and the resulting mixture was refluxed for 12 hours. The reaction mixture was concentrated on rotavapor and the residue was diluted with ethyl acetate (50 ml). The ethyl acetate solution was washed successively with water, saturated sodium bicarbonate (NaHCO$_3$), water, and dried over anhydrous magnesium sulfate (MgSO$_4$). Evaporation of the solvent gave the target ester 13a as colorless oil in 90% yield (1.78 g). The ester 13a was taken to next step without any further purification. $^1$H NMR (400 MHz, CDCl$_3$): δ 1.30 (3H, t, J=7.2 Hz); 4.29 (2H, t, J=7.2 Hz); 4.83 (2H, s); 7.53 (1H, m); 7.69 (1H, broad d); 7.90 (1H, broad d); 8.01 (1H, s).

Example 18

Isopropyl 3-(chloromethyl)benzoate 13b was prepared by reacting 3-(chloromethyl)benzoic acid 23 with isopropanol according to the procedure described for the compound 13a in Example 17 (scheme 7). The benzoate 13b was isolated as colorless oil in 87% yield (1.85 g). $^1$H NMR (400 MHz, CDCl$_3$): δ 1.37 (6H, m); 4.62 (2H, s); 5.27 (2H, m); 7.43 (1H, m); 7.57 (1H, broad d); 7.98 (1H, broad d); 8.04 (1H, s).

Example 19

Ethyl 4-(chloromethyl)benzoate 13c was prepared by reacting 4-(chloromethyl)benzoic acid 24 with ethanol according to the procedure described for the compound 13a in Example 17 (scheme 7). The benzoate 13bc was isolated as colorless oil in 91% yield (1.80 g). $^1$H NMR (400 MHz, CDCl$_3$): δ 1.37 (3H, t, J=7.2 Hz); 4.46 (2H, t, J=7.2 Hz); 4.58 (2H, s); 7.42 (1H, m); 7.44 (1H, broad d); 8.00 (1H, broad d); 8.02 (1H, s).

Example 20

Isopropyl 4-(chloromethyl)benzoate 13d was prepared by reacting 4-(chloromethyl)benzoic acid 24 with isopropanol according to the procedure described for the compound 13a in Example 16 (scheme 7). The benzoate 13d was isolated as colorless oil in 89% yield (1.90 g). $^1$H NMR (400 MHz, CDCl$_3$): δ 1.35 (6H, m); 4.59 (2H, s); 5.25 (2H, m); 7.42 (1H, m); 7.44 (1H, broad s); 8.00 (1H, broad s); 8.02 (1H, s).

Example 21

Ethyl 4-(3-(chloromethyl)benzamido)butanoate 13e (Scheme 8)

To a stirred solution of 3-(chloromethyl)benzoic acid 24 (0.01 mol) and N-hydroxysuccinimide (0.012 mol) in acetonitrile (25 ml) at room temperature was added N,N-dicyclohexylcarbodiimide (0.012 mol). The resulting mixture was stirred at room temperature for 3 h. The reaction mixture was filtered and the precipitate was washed with acetonitrile (15 ml×2). To the combined filtrate, ethyl 4-aminobutyrate hydrochloride 26 (0.01 mol) was added at room temperature followed by a solution of sodium bicarbonate (NaHCO$_3$) in water (15 ml). The resulting mixture was stirred for 12 hours. The reaction mixture was concentrated on rotavapor and the residue was diluted with ethyl acetate (50 ml). The mixture was washed with water (25 ml×2), dried over sodium sulfate (Na$_2$SO$_4$) and evaporated the solvent. The residue was purified by passing through a short silica gel column using 0 to 50% ethyl acetate and hexane as eluent to give the target compound 13e as colorless oil in 79% yield (2.24 g). $^1$H NMR (400 MHz, CDCl$_3$): δ 1.24 (3H, broad t); 1.96 (2H, m); 2.44

(2H, m); 3.51 (2H, m); 4.13 (2H, broad q); 4.60 (2H, s); 6.65 (1H, broad s); 7.45 (2H, m); 7.77 (2H, m); MS (ESI): m/z=284.0 (M+H$^+$).

Example 22

Ethyl 3-(4-(chloromethyl)benzamido)propanoate 13f was prepared by coupling 4-(chloromethyl)benzoic acid 24 with ethyl 3-aminopropionate 25 according to the procedure described for the compound 13e in Example 21 (Scheme 8). The compound 13f was isolated as colorless oil in 84% yield (2.26 g). $^1$H NMR (400 MHz, CDCl$_3$): δ 1.26 (3H, t, J=7.2 Hz); 2.64 (2H, m); 3.72 (2H, m); 4.14 (2H, q, J=7.2 Hz); 4.61 (2H, s); 6.89 (1H, broad s); 7.53 (1H, s); 7.67 (1H, s); 7.70 (1H, s). 7.80 (1H s). MS (ESI): m/z=270.00 (M+H$^+$).

Example 23

Ethyl 4-(4-(chloromethyl)benzamido)butanoate 13g was prepared by coupling 4-(chloromethyl)benzoic acid 24 with ethyl 4-aminobutyrate 26 according to the procedure described for the compound 13e in Example 21 (Scheme 8). The compound 13g was isolated as colorless oil in 89% yield (2.52 g). $^1$H NMR (400 MHz, CDCl$_3$): δ 1.24 (3H, t, J=6.8 Hz); 1.96 (2H, quint, J=7.2 Hz); 2.44 (2H, t, J=7.2 Hz); 3.52 (2H, t, J=7.2 Hz); 4.10 (2H, q, J=6.8 Hz); 4.60 (2H, s); 6.62 (1H, broad s); 7.44 (1H, s); 7.46 (1H, s); 7.76 (1H, s); 7.78 (1H, s). MS (ESI): m/z=284.00 (M+H$^+$).

Example 24

Ethyl 2-(3-(hydroxymethyl)phenoxy)acetate 29a (Scheme 9)

To a stirred suspension of potassium carbonate (0.02 mol) in acetone (25 ml) was added 3-(hydroxymethyl)phenol 27a (0.01 mol) and ethyl bromoacetate 28a (0.012) and the resulting mixture was refluxed for 12 hours. The reaction mixture was cooled to room temperature and filtered. The filtrate was concentrated on rotavapor and the residue was diluted with ethyl acetate (50 ml). The ethyl acetate solution was washed successively with water, saturated sodium bicarbonate (NaHCO$_3$), water, and then dried over anhydrous sodium sulfate (Na$_2$SO$_4$). After evaporation of the solvent the crude product was passed though a short silica gel column using 0-50% ethyl acetate and hexane as eluent to give the pure ester 29a as colorless oil in 97% yield (2.03 g). $^1$H NMR (400 MHz, CDCl$_3$): δ 1.23 (3H, t, J=6.8 Hz); 3.36 (1H, broad s); 4.19 (2H, q, J=6.8 Hz); 4.44 (2H, s); 6.74 (1H, broad d); 6.87 (1H, m); 7.18 (1H, t, J=8 Hz). MS (ESI): m/z=233.00 (M+Na$^+$).

Example 25

Ethyl 4-(4-(hydroxymethyl)phenoxy)butanoate 29b was prepared by reacting 4-(hydroxymethyl)phenol 27b with ethyl 4-bromobutyrate 28b according to protocol described for the compound 29a in Example 24 (Scheme 9). The ester 29b was isolated as colorless oil 96% yield (2.26 g). $^1$H NMR (400 MHz, CDCl$_3$): δ 1.24 (3H, t, J=7.2 Hz); 2.07 (2H, m); 2.15 (2H, t, J=7.2 Hz)); 3.97 (2H, t, J=6.4 Hz); 4.10 (2H, q, J=7.2 Hz); 4.59 (2H, s); 6.88 (1H, s); 6.87 (1H, s); 7.24-7.27 (2H, m).

Example 26

Ethyl 2-(3-(chloromethyl)phenoxy)acetate 13h (Scheme 9)

Thionyl chloride (0.01 mole) was added to an ice cold ester 29a (0.005 mole) and the resulting mixture was stirred at room temperature for 5 hours. The progress of the reaction was monitored by TLC. The reaction mixture was poured into ice cold water (50 ml). The mixture was extracted with ethyl acetate (25 ml×2), washed with water (25 ml), dried over anhydrous magnesium sulfate (MgSO$_4$) and evaporated the solvent. The residue was passed through a short silica gel column using 0-50% ethyl acetate and hexane as eluent to give the pure chloride 13h as color less oil in 86% yield (0.98 g). $^1$H NMR (400 MHz, CDCl$_3$): δ 1.26 (3H, t, J=6.8 Hz); 4.27 (2H, q, J=6.8 Hz); 4.28 (2H, s); 6.85 (1H, broad d); 6.99 (1H, m); 7.26 (1H, m). MS (ESI): m/z=253.10 (M+H$^+$).

Example 27

Ethyl 4-(4-(chloromethyl)phenoxy)butanoate 13i was prepared from 29b according to the protocol described for the compound 13h in Example 26 (Scheme 9). The title chloride 13i was isolated as colorless oil in 96% yield (1.25 g). $^1$H NMR (400 MHz, CDCl$_3$): δ 1.24 (3H, t, J=7.2 Hz); 2.06 (2H, m); 2.18 (2H, t, J=7.2 Hz)); 4.00 (2H, t, J=6.4 Hz); 4.14 (2H, q, J=7.2 Hz); 4.54 (2H, s); 6.83 (1H, s); 6.86 (1H, s); 7.27 (1H, m); 7.29 (1H, s). MS (ESI): m/z=258.10 (M+H$^+$).

Example 28

Ethyl 3-(2-chloroacetamido)propanoate 31 (Scheme 10)

To a stirred solution of ethyl 3-aminopropionate hydrochloride 25 (0.01 mole) and triethylamine (0.02 mole) in DCM (25 ml) at ice-bath temperature was added dropwise a solution of chloroacetyl chloride 30 (0.01 mol) in DCM (5 ml). The resulting mixture was stirred at ice-bath temperature for 1 hour and at room temperature for 4 hours. The reaction mixture was poured into ice-cold water (50 ml). The mixture was extracted with DCM (25 ml×2), washed with water (25 ml), dried over sodium sulfate (Na$_2$SO$_4$) and evaporated the solvent. The residue was filtered through a short silica gel column using 0-50% ethyl acetate and hexane as eluent to give the pure chloroamide 31 as light yellow oil in 99% yield (1.91 g). $^1$H NMR (400 MHz, CDCl$_3$): δ 1.16 (3H, t, J=6.4 Hz); 2.45 (2H, t, J=6.8 Hz); 3.30 (2H, q, J=6.8 Hz); 4.01 (2H, s); 4.05 (2H, q, J=6.4 Hz); 8.27 (1H broad s).

Example 29

Ethyl 3-(2-(3-(hydroxymethyl)phenoxy)acetamido) propanoate 32 (Scheme 10)

To a stirred suspension of potassium carbonate (0.02 mol) in acetone (25 ml) was added 3-(hydroxymethyl)phenol 27a (0.01 mol) and chloroamide 31 (0.012) and the resulting mixture was refluxed for 12 hours. The reaction mixture was cooled to room temperature and filtered. The filtrate was concentrated on rotavapor and the residue was diluted with ethyl acetate (50 ml). The ethyl acetate solution was washed successively with water, saturated sodium bicarbonate (NaHCO$_3$), water, and then dried over anhydrous sodium sulfate (Na$_2$SO$_4$). After evaporaton of the solvent the crude product was passed though a short silica gel column using 0-100% ethyl acetate and hexane as eluent to give the pure ester 32 as colorless oil in 95% yield (2.67 g). $^1$H NMR (400 MHz, CDCl$_3$): δ 1.22 (3H, m); 2.52 (2H, broad t); 3.53 (2H, broad t); 3.95 (2H, broad s); 4.08 (2H, m); 4.52 (2H, s); 6.67-6.92 (2H m); 6.86 (1H, s); 7.10 (1H, m); 7.28 (1H, broad s). MS (ESI): m/z=304.10 (M+Na$^+$).

Example 30

Ethyl 3-(2-(3-(chloromethyl)phenoxy)acetamido) propanoate 13j (Scheme 10)

Thionyl chloride (0.01 mole) was added to an ice cold ester 32 (0.005 mole) and the resulting mixture was stirred at room temperature for 5 hours. The progress of the reaction was monitored by TLC. The reaction mixture was poured into ice cold water (50 ml). The mixture was extracted with ethyl acetate (25 ml×2), washed with water (25 ml), dried over anhydrous magnesium sulfate ($MgSO_4$) and evaporated the solvent. The residue was passed through a short silica gel column using 0-100% ethyl acetate and hexane as eluent to give the pure chloride 13j as color less oil in 47% yield (0.70 g). $^1$H $^1$H NMR (400 MHz, $CDCl_3$): δ 1.25 (3H, t, J=6.8 Hz); 2.56 (2H, t, J=6 Hz); 3.57 (2H, m); 4.05 (2H, s); 4.16 (2H, q, J=6.8 Hz); 4.51 (2H, s); 6.79-6.82 (2H, m); 6.89 (1H, s); 7.18 (1H, m); MS (ESI): MS (ESI): m/z=300.00 (M+H$^+$).

Example 31

Ethyl 3-(4-hydroxy-3-methoxyphenyl)acrylate 35a (Scheme 11)

A solution of vanilin (0.05 mol, 7.60 g) and commercially available Wittig ylide, ethyl (triphenylphosphoranylidine)-acetate (0.06 mol, 20.90 g) in toluene (75 ml) was refluxed for 2 hours. The progress of the reaction was monitored by TLC. The reaction mixture was concentrated in vacuum and the residue was dissolved in ethyl acetate (100 ml). The ethyl acetate solution was washed with water (50 ml×2), dried over magnesium sulfate ($MgSO_4$) and evaporated the solvent. The residue was purified by silica gel chromatography using 0-50% gradient of ethyl acetate and hexane as eluent to give the title compound 35a as light yellow thick liquid in 80% yield (8.90 g). $^1$H NMR (300 MHz, $CDCl_3$): δ 1.33 (3H, t, J=9 Hz); 3.90 (3H, s); 4.25 (2H, q, J=9 Hz); 6.30 (1H, d, J=24 Hz); 7.01 (3H, m); 7.60 (1H, d, J=24 Hz). $^{13}$C NMR (75 hz, $CDCl_3$): δ 13.59; 55.13; 59.67; 108.64; 114.07; 114.71; 122.26; 126.18; 144.06; 146.11; 147.27; 166.70.

Example 32

Ethyl 3-(3-hydroxy-4-methoxyphenyl)acrylate 35b was prepared from isovanilin according to the protocol described for the preparation of compound 35a in Example 31 (Scheme 11). Isolated as light yellow liquid in 75% yield (8.25 g). $^1$H NMR (300 MHz, $CDCl_3$): δ 1.30 (3H, broad t); 3.85 (3H, s); 4.20 (2H, broad q); 6.28 (1H, d, J=24 Hz); 6.99 (1H, m); 7.13 (1H, m); 7.19 (1H, s); 7.58 (1H, d, J=24 Hz). $^{13}$C NMR (75 hz, $CDCl_3$): δ14.01; 55.59; 60.15; 110.42; 112.97; 116.31; 121.50; 127.20; 144.38; 147.51; 148.59; 167.22.

Example 33

6-Hydroxy-5-methoxy-2,3-dihydro-1H-inden-1-one 18a (Scheme 11)

To a stirred suspension of 2.00 g of palladium, 10 wt % on activated carbon in methanol (30 ml) was added compound 35a (0.03 mol, 6.66 g) and then subjected to hydrogenation on Parr shaker at 60 psi for 15 hour. The reaction mixture was filtered through a Celite® pad and the filtrate was concentrated under vacuum to give the title compound in 90% (6.00 g) yield. The crude ester was subjected to saponification using 1N potassium hydroxide in THF at room temperature to get the corresponding carboxylic acid in nearly quantitative yield. The carboxylic acid was heated in concentrated sulfuric acid at 90° C. for 4 h to get the title compound as light brown solid in 70% (3.50 g) overall yield. $^1$H NMR (300 MHz, $CDCl_3$): δ 2.67 (2H, m); 3.08 (2H, m); 3.98 (3H, s); 6.89 (1H, s); 7.15 (1H, s); 7.32 (1H, s). $^{13}$C NMR (75 Hz, $CDCl_3$): δ 24.59; 35.62; 55.04; 106.57; 106.86; 128.76; 145.58; 149.32; 153.85; 206.74.

Example 34

5-Hydroxy-6-methoxy-2,3-dihydro-1H-inden-1-one 18b was prepared from 35b V according to the protocol described for the preparation of compound 18a in Example 33 (Scheme 11). Isolated as light brown powder in 67% overall yield (3.55 g). $^1$H NMR (300 MHz, $CDCl_3$): δ 2.69 (2H, m); 3.03 (2H, m); 3.92 (3H, s); 4.28 (1H, broad s); 6.92 (1H, s); 7.17 (1H, s). $^{13}$C NMR (75 Hz, $CDCl_3$): δ 24.65; 35.86; 55.05; 103.68; 111.00; 127.98; 147.67; 151.32; 153.72; 206.88.

Example 35

(1-Benzylpiperidin-4-yl)methanol 40 (Scheme 12)

To a stirred solution of 4-(hydroxymethyl)piperidine 38 (0.01 mol) and DIEA (0.02 mol) in anhydrous acetonitrile (20 ml) was added a solution of benzylbromide 39 (0.012 mol) in anhydrous acetonitrile (5 ml) at room temperature. The resulting mixture was heated at 55-60° C. for 12 hours. The progress of the reaction was monitored by TLC. The reaction mixture was concentrated on rotavapor and the residue was diluted with ethyl acetate (50 ml). The resulting ethyl acetate solution was washed with water, dried over anhydrous sodium sulfate ($Na_2SO_4$) and evaporated the solvent. The residue was purified by silica gel column chromatography using a gradient of 0 to 100% ethyl acetate and hexane to get the title piperidine 40 in 98% yield (2.00 g) yield. $^1$H NMR (400 MHz, CDCl3): δ 1.26-1.33 (2H, m); 1.43-1.52 (1H, m); 1.70 (2H, broad d); 1.96 (2H, broad t); 2.90 (2H, broad d); 3.48 (2H, s); 3.49 (2H, s); 7.30 (5H, m). MS (ESI): m/z=206.20 (M+H$^+$).

Example 36

1-Benzyl-4-(chloromethyl)piperidine 21 (Scheme 12)

Thionyl chloride (0.01 mole) was added to an ice cold ester 40 (0.005 mole) and the resulting mixture was stirred at room temperature for 5 hours. The progress of the reaction was monitored by TLC. The reaction mixture was poured into ice cold water (50 ml). The mixture was extracted with ethyl acetate (25 ml×2), washed with water (25 ml), dried over anhydrous magnesium sulfate ($Na_2SO_4$) and evaporated the solvent. The residue was passed through a short silica gel column using 0-100% ethyl acetate and hexane as eluent to give the pure chloride 21 as color less oil in 66% yield (0.74 g). $^1$H $^1$H NMR (400 MHz, $CDCl_3$): δ 1.24-1.33 (2H, m); 1.43-1.60 (1H, m); 1.77 (2H, broad d); 1.93 (2H, broad t); 2.92 (2H, broad d); 3.34 (2H, s); 3.50 (2H, s); 7.29 (5H, m). MS (ESI): m/z=224.74 (M+H$^+$).

While the invention has been particularly shown and described with reference to a preferred embodiment and various alternate embodiments, it will be understood by persons skilled in the relevant art that various changes in form and details can be made therein without departing from the spirit and scope of the invention. All printed patents and publications referred to in this application are hereby incorporated herein in their entirety by this reference

What is claimed is:

1. An indanone derivative of structural Formula (III):

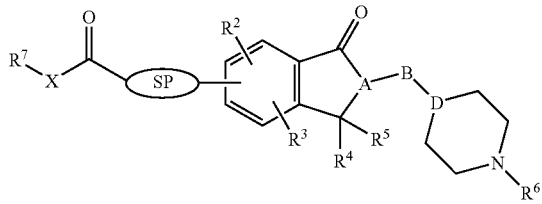

Formula III or a pharmaceutically acceptable salt thereof, wherein:
X is O or NH;
SP is a spacer, and wherein the spacer is —O-alkylene-, or -oxyacetamidoalkylene-;
A and D are CH;
B is —$(CH_2)_n$—, wherein n is an integer between 1 and 5;
$R^2$ is H, alkoxy, or halogen;
$R^3$ is H,
$R^4$ and $R^5$ are independently H or alkyl;
$R^6$ is arylalkyl or substituted arylalkyl; and
$R^7$ is H or alkyl.

2. The derivative of claim 1, wherein SP is —O-alkylene-.

3. The indanone derivative of structural Formula (V) according to claim 1:

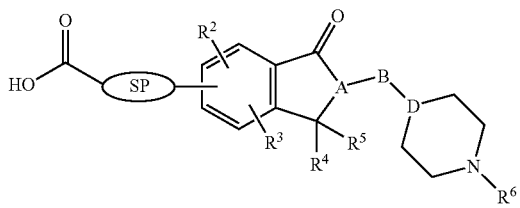

Formula V or a pharmaceutically acceptable salt thereof.

4. A pharmaceutical composition comprising the compound of claim 1 and a pharmaceutically acceptable excipient.

5. The pharmaceutical composition of claim 4, wherein the excipient is for oral, mucosal, rectal, parenteral, transdermal, or subcutaneous administration.

6. An indanone derivative of Compound 16,

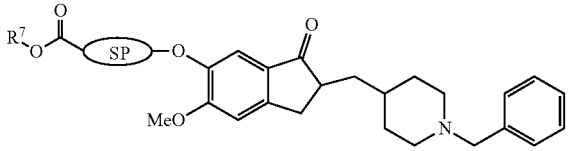

16 wherein SP is $CH_2$, $CH_2CH_2CH_2$, or $CH_2CH_2CH_2NHC(O)CH_2$.

7. The indanone derivative according to claim 6, wherein SP is $CH_2CH_2CH_2$ and $R^7$ is ethyl or tert-butyl.

8. An indanone derivative of Compound 10,

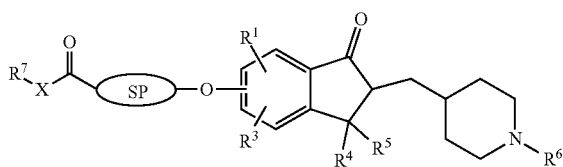

10 wherein X is O or NH,
SP is alkylene,
$R^1$ is H, alkoxy, or halogen,
$R^3$ is H,
$R^4$ and $R^5$ are independently H or alkyl;
$R^6$ is arylalkyl or substituted arylalkyl; and
$R^7$ is H or alkyl.

9. An indanone derivative of Compound 14,

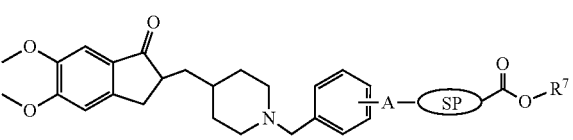

14 wherein A is O, C(O)O, CONH, or $OCH_2C(O)NH$, SP is alkylene, and $R^7$ is H or alkyl.

10. An indanone derivative, which is

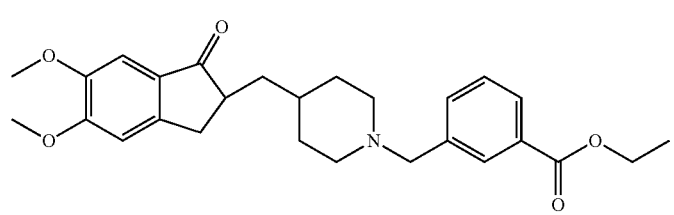

14a

14b
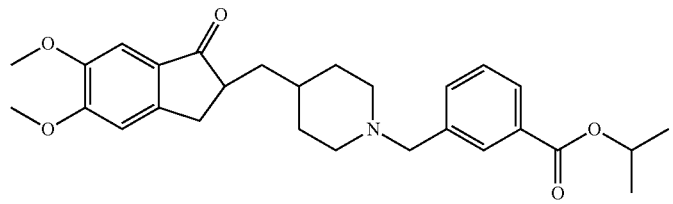
14c
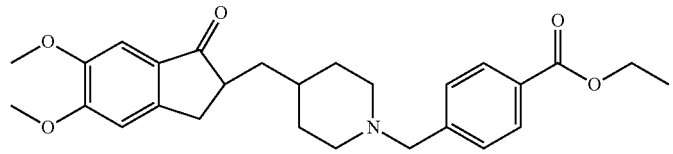
14d
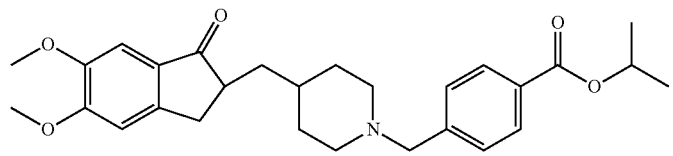
14e
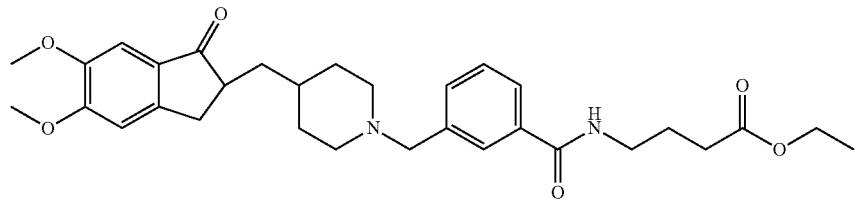
14f
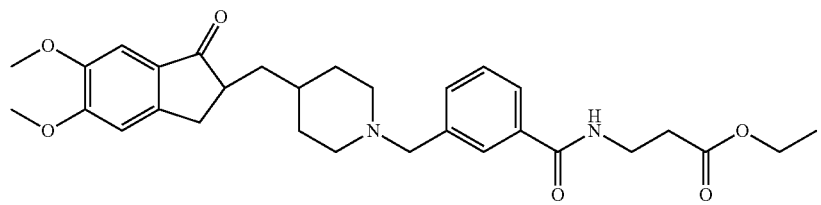
14g
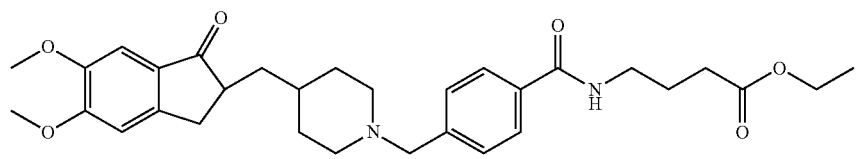
14h
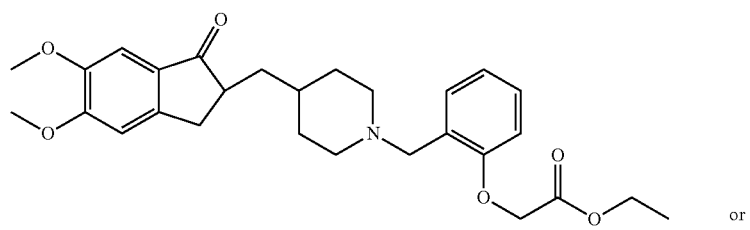
or
14i
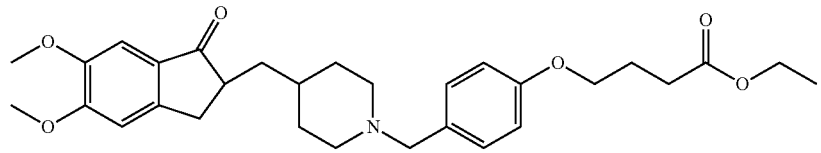

14j
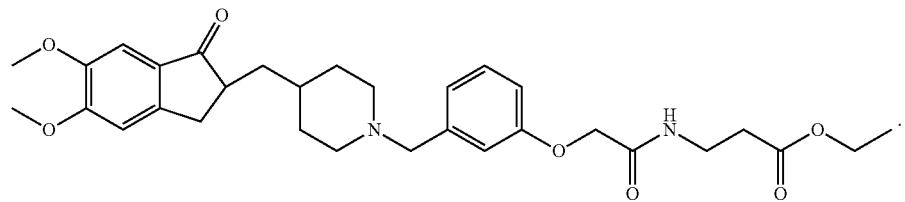
* * * * *